US008905034B2

(12) United States Patent
Goranov et al.

(10) Patent No.: US 8,905,034 B2
(45) Date of Patent: Dec. 9, 2014

(54) ERGONOMIC PROTECTIVE AIR FILTRATION DEVICES AND METHODS FOR MANUFACTURING THE SAME

(75) Inventors: Konstantin Goranov, Atkinson, NH (US); Albena Milencheva, Atkinson, NH (US)

(73) Assignee: Salutaris LLP, Boston, MA (US)

( * ) Notice: Subject to any disclaimer, the term of this patent is extended or adjusted under 35 U.S.C. 154(b) by 385 days.

(21) Appl. No.: 13/290,972

(22) Filed: Nov. 7, 2011

(65) Prior Publication Data

US 2012/0111344 A1 May 10, 2012

Related U.S. Application Data

(60) Provisional application No. 61/410,678, filed on Nov. 5, 2010.

(51) Int. Cl.

| | |
|---|---|
| ***A41D 13/00*** | (2006.01) |
| ***A42B 1/00*** | (2006.01) |
| ***A42B 1/08*** | (2006.01) |
| ***A41D 13/12*** | (2006.01) |
| ***A62B 18/08*** | (2006.01) |
| ***A61M 16/00*** | (2006.01) |
| ***A62B 18/02*** | (2006.01) |
| ***A61F 5/37*** | (2006.01) |
| ***A61F 11/00*** | (2006.01) |
| ***A61B 19/00*** | (2006.01) |
| ***A41D 13/11*** | (2006.01) |
| ***A62B 23/02*** | (2006.01) |

(52) U.S. Cl.

CPC .......... *A41D 13/1115* (2013.01); *A62B 23/025* (2013.01)

USPC ....... 128/863; 2/9; 2/424; 2/456; 128/201.17; 128/201.19; 128/201.23; 128/203.29; 128/205.25; 128/206.12; 128/206.13; 128/206.19; 128/206.21; 128/206.28; 128/846; 128/857

(58) Field of Classification Search

USPC ............. 128/201.17, 201.19, 201.23, 203.29, 128/205.25, 206.12, 206.13, 206.19, 128/206.21, 206.28, 846, 857, 863; 2/9, 2/424, 456

See application file for complete search history.

(56) References Cited

U.S. PATENT DOCUMENTS

| | | | |
|---|---|---|---|
| 3,664,335 | A | 5/1972 | Boucher et al. |
| D248,497 | S | 7/1978 | Slosek |

(Continued)

FOREIGN PATENT DOCUMENTS

| | | |
|---|---|---|
| CA | 2170112 | 8/1996 |
| CA | 2366380 | 10/2000 |

(Continued)

OTHER PUBLICATIONS

PCT International Search Report based on PCT/US2011/059640 dated Mar. 16, 2012.

(Continued)

*Primary Examiner* — Victoria J Hicks
*Assistant Examiner* — Brandon L Jackson
(74) *Attorney, Agent, or Firm* — McLane, Graf, Raulerson & Middleton, PA

(57) ABSTRACT

Ergonomic protective air filtration devices and methods for manufacturing the same are disclosed herein. An ergonomic protective air filtration device includes a stack of at least two layers of an air permeable material, the stack forming a body, a periphery, and a back; a plurality of intersecting three-dimensional V-shaped pleats extending from the periphery and into the stack of layers, so the back of the device defines a breathing chamber adapted to cover a mouth and a nose of the wearer; and a retaining means engaging the body of the device to secure the device to a face of the wearer and to create the breathing chamber. The ergonomic protective air filtration device provides protection against contaminated droplets, fluid splashes, solid particulates, pathogenic microorganisms, or aerosoled air pollutions.

15 Claims, 19 Drawing Sheets

(56) References Cited

U.S. PATENT DOCUMENTS

| | | | | |
|---|---|---|---|---|
| D267,985 | S | | 2/1983 | Huber |
| D273,145 | S | | 3/1984 | Ponsi |
| D287,649 | S | | 1/1987 | Zdrok et al. |
| 5,374,458 | A | | 12/1994 | Burgio |
| 5,419,318 | A | | 5/1995 | Tayebi |
| D368,960 | S | | 4/1996 | Lanford |
| 5,558,089 | A | | 9/1996 | Castiglione |
| 5,561,863 | A | | 10/1996 | Carlson, II |
| 5,611,938 | A | | 3/1997 | Smolik et al. |
| 5,620,545 | A | * | 4/1997 | Braun et al. .................. 156/205 |
| D390,652 | S | | 2/1998 | Parker |
| 6,041,782 | A | | 3/2000 | Angadjivand et al. |
| 6,116,236 | A | | 9/2000 | Wyss |
| 6,224,579 | B1 | | 5/2001 | Modak et al. |
| D443,927 | S | | 6/2001 | Chen |
| D464,726 | S | | 10/2002 | Wolfe |
| 6,474,336 | B1 | | 11/2002 | Wolfe |
| 6,585,989 | B2 | | 7/2003 | Herbst et al. |
| 6,596,906 | B2 | | 7/2003 | Baumann et al. |
| 6,715,489 | B2 | | 4/2004 | Bostock et al. |
| 6,843,784 | B2 | | 1/2005 | Modak et al. |
| D511,209 | S | | 11/2005 | Callan |
| 7,131,442 | B1 | | 11/2006 | Kronzer et al. |
| 7,171,967 | B2 | | 2/2007 | Brunell et al. |
| 7,185,653 | B2 | | 3/2007 | Lee |
| 7,210,482 | B2 | | 5/2007 | Huang et al. |
| 7,290,545 | B2 | | 11/2007 | Kleman et al. |
| 7,559,968 | B2 | | 7/2009 | Bolduc |
| 7,766,015 | B2 | | 8/2010 | Harold et al. |
| 7,802,572 | B2 | | 9/2010 | Hahne |
| D638,171 | S | | 5/2011 | Goranov et al. |
| 8,052,821 | B2 | | 11/2011 | Cheng |
| D658,334 | S | | 4/2012 | Goranov et al. |
| 2001/0010016 | A1 | | 7/2001 | Modak et al. |
| 2002/0038055 | A1 | | 3/2002 | Baumann et al. |
| 2002/0106413 | A1 | | 8/2002 | Herbst et al. |
| 2003/0125413 | A1 | | 7/2003 | Herbst et al. |
| 2003/0125583 | A1 | | 7/2003 | Baumann et al. |
| 2005/0124725 | A1 | | 6/2005 | Modak et al. |
| 2005/0131100 | A1 | | 6/2005 | Herbst et al. |
| 2006/0130841 | A1 | | 6/2006 | Spence et al. |
| 2007/0048344 | A1 | | 3/2007 | Yahiahoui et al. |
| 2007/0231391 | A1 | | 10/2007 | Bracken et al. |
| 2008/0295843 | A1 | | 12/2008 | Haas |
| 2010/0218774 | A1 | | 9/2010 | Flaherty |

FOREIGN PATENT DOCUMENTS

| | | |
|---|---|---|
| EM | 001853870-000 | 4/2011 |
| EP | 1 190 622 | 3/2002 |
| EP | 2 298 419 | 3/2011 |
| GB | 2456263 | 5/2011 |
| JP | 4990228 | 1/2012 |
| WO | WO 2005/067895 | 7/2005 |
| WO | WO 2006/034227 | 3/2006 |
| WO | WO 2008/052342 | 5/2008 |
| WO | WO 2009/026725 | 3/2009 |
| WO | WO 2010/034057 | 4/2010 |
| WO | WO 2012/030798 | 3/2012 |

OTHER PUBLICATIONS

"Safety & Industrial 2009 Buyer's Guide," *LSS*, Disposable Respirators, pp. 142-151, 340, 851 (Jan. 2009).

"2009-2010 Buyer's Guide: Hard Hats, Safety Glasses, Ear Plugs, Respirators, Faceshields . . . " *R3 Safety*, Respiratory Protection: Disposables, pp. 104-112 (Jan. 2009).

"Product Catalog: Total Solutions to Health Care," *INTCO Healthcare, FIME Expo*, Nonwoven Disposables, pp. 5-10 (Aug. 2010).

"2010-2011 Catalogue of Plus Medical," *Foshan Nanhai Plus Medical Co., Ltd., FIME Expo*, pp. 17 (Aug. 2010).

"Weini Product Brochure," *Weinida Nonwoven Textiles Co., Ltd., NSC Congress & Expo* (Oct. 2009).

"MaskEnomics—A Reference Guide to Proper Mask Selection," *Crosstex* (Apr. 2010).

"3M VFlex Particulate Respirators 9105 and 9105S, N95," *3M, NSC Congress & Expo* (Oct. 2010).

"Respiratory Protection: Product Guide 2008 01/10 SPR670031," *NSC Congress & Expo*, Disposable Respirators, pp. 3-15 (Jan. 2010).

"Dashengmask: Health Talisman," *Shanghai Dasheng Health Products Manufacture Co., Ltd., NSC Congress & Expo*, pp. 27-31 (Oct. 2010).

"Fitseal FS300, FS400 & FS500 Series Respirators," *Wein Products, Inc., NSC Congress & Expo* (Oct. 2010).

"Kimberly-Clark PFR95 N95 Particulate Filter Respirators," *Kimberly-Clark* (Mar. 2007).

"Moldex Hearing & Respiratory Protection Product Catalog 9700-748," *Moldex-Metric, Inc.*, pp. 2-7 (Sep. 2009).

"Gerson Smart-Mask Particulate Respirators: A New Level of Design, Function and Performance," *Gerson Co., Inc.* (Jan. 2007).

"Gateway Safety, Inc.: Where Safety Meets Style," *Gateway Safety, Inc.*, Respiratory Protection Disposable Respirators, pp. 26-27 (Jan. 2009).

* cited by examiner

Nonwoven fabric panel - size S

Nonwoven fabric panel - size M

Nonwoven fabric panel - size L

ERGONOMIC PROTECTIVE AIR FILTRATION DEVICES AND METHODS FOR MANUFACTURING THE SAME

CROSS REFERENCE TO RELATED APPLICATIONS

This application is related to and claims the benefit of priority from U.S. Provisional Application No. 61/410,678, filed on Nov. 5, 2011, the entirety of which is incorporated herein by reference.

FIELD

The presently disclosed embodiments relate to the field of personal protective devices for respiratory protection. More particularly, it concerns an Ergonomic Protective Device and methods for manufacturing the same.

BACKGROUND

There are varieties of air filtering and protective devices known in the art whose design and performance characteristics are tailored in accordance to the approved standards and field of application. Generally known as facemasks, surgical masks, procedural masks, or personal respirators, these protective devices are constructed in different sizes and shapes, are made of different types of permeable materials, are provided with different types of donning or attachments, and are formed with one or several filtering layers in order to achieve a specific level of protection.

In the medical and healthcare field, surgical masks are typically used to protect the wearers and their surrounding environment from transfer of microorganisms, bodily fluids, particulate materials and other contaminants either dispersed in the ambient air or emitted by the wearer.

Dust filtering and specialty respirator masks are also worn in industrial settings, on construction sites, and in modern agriculture and food processing plants in order to prevent workers from inhaling powder substances, aerosols and airborne particles.

A drawback commonly found with existing masks and respirators is that there are constraints and restrictions imposed on the natural breathing cycle and facial articulation, which may prevent the wearer from speaking naturally and clearly, or most importantly, may be bothersome and uncomfortable in cases of prolonged use. Furthermore, certain protective masks may compromise the seal of the mask against the wearer's face with even a slight movement of the facial muscles.

Other common disadvantages of high barrier masks and respirators include heat generated in the mask's breathing chamber, the inherent difficulty for the wearer to inhale and exhale easily through the mask filtration media, and the restricted downward field of vision when wearing respirators. To avoid restricted air flow through the protective device, wearers of the device commonly do not attach the device properly to their faces, thus creating a great potential for harmful exposure to airborne contaminants.

Although there are several styles of respirator and protective masks designed for specific fields of application, most masks and respirators present one or more of the drawbacks described. Accordingly, there is a persisting need in the art for an improved design and construction of ergonomic respirators and protective facemasks.

Though existing facemasks may be effective in blocking splashes, large droplets and particles, they typically fit loosely to the face, thereby failing to provide complete protection from germs and other contaminants. Alternatively, the most common N-95 respirators in North America (the N-95 respirator is one of seven types of particulate filtering face-piece respirators that filters at least 95 percent of airborne particles according to National Institute for Occupational Safety and Health (NIOSH) tests), when properly fitted, exceed the protection levels of regular facemasks but also create significant resistance to normal breathing and restrain natural face movement.

SUMMARY

Ergonomic protective air filtration devices and methods for manufacturing the same are disclosed herein.

According to aspects illustrated herein, there is provided an ergonomic protective air filtration device includes an arrangement of at least two layers of an air permeable material, the arrangement having a periphery, an inner side and an outer side; a plurality of three-dimensional V-shaped pleats extending from the periphery and into the arrangement of layers to form a convex body; and a retaining means engaging the convex body of the device to secure the device to a face of a wearer and to create a breathing chamber on the inner side of the device.

According to aspects illustrated herein, there is provided an ergonomic protective air filtration device includes a stack of at least two layers of an air permeable material, the stack forming a body, a periphery, and a back; a plurality of intersecting three-dimensional V-shaped pleats extending from the periphery and into the stack of layers, so the back of the device defines a breathing chamber adapted to cover a mouth and a nose of the wearer; and a retaining means engaging the body of the device to secure the device to a face of the wearer and to create the breathing chamber.

According to aspects illustrated herein, there is provided a method for constructing an ergonomic protective air filtration device includes stacking at least two layers, each made of an air permeable material, into a stack forming a body, a periphery, and a back; forming, with the stack of layers, a plurality of three-dimensional V-shaped pleats extending from the periphery, so that the back of the device defines a breathing chamber adapted to cover a nose and a mouth of a wearer; joining the layers of the stack and the pleats at the periphery of the device and at a plurality of specific points throughout the stack of layers; and affixing a retaining means to the periphery of the device for retaining the device to a face of the wearer and creating a breathing chamber.

BRIEF DESCRIPTION OF THE DRAWINGS

Other objects, advantages and features of the presently disclosed embodiments will become more apparent upon reading the following non-restrictive description of embodiments thereof, given for the purpose of exemplification only, with reference to the accompanying drawings in which.

Figure 1:
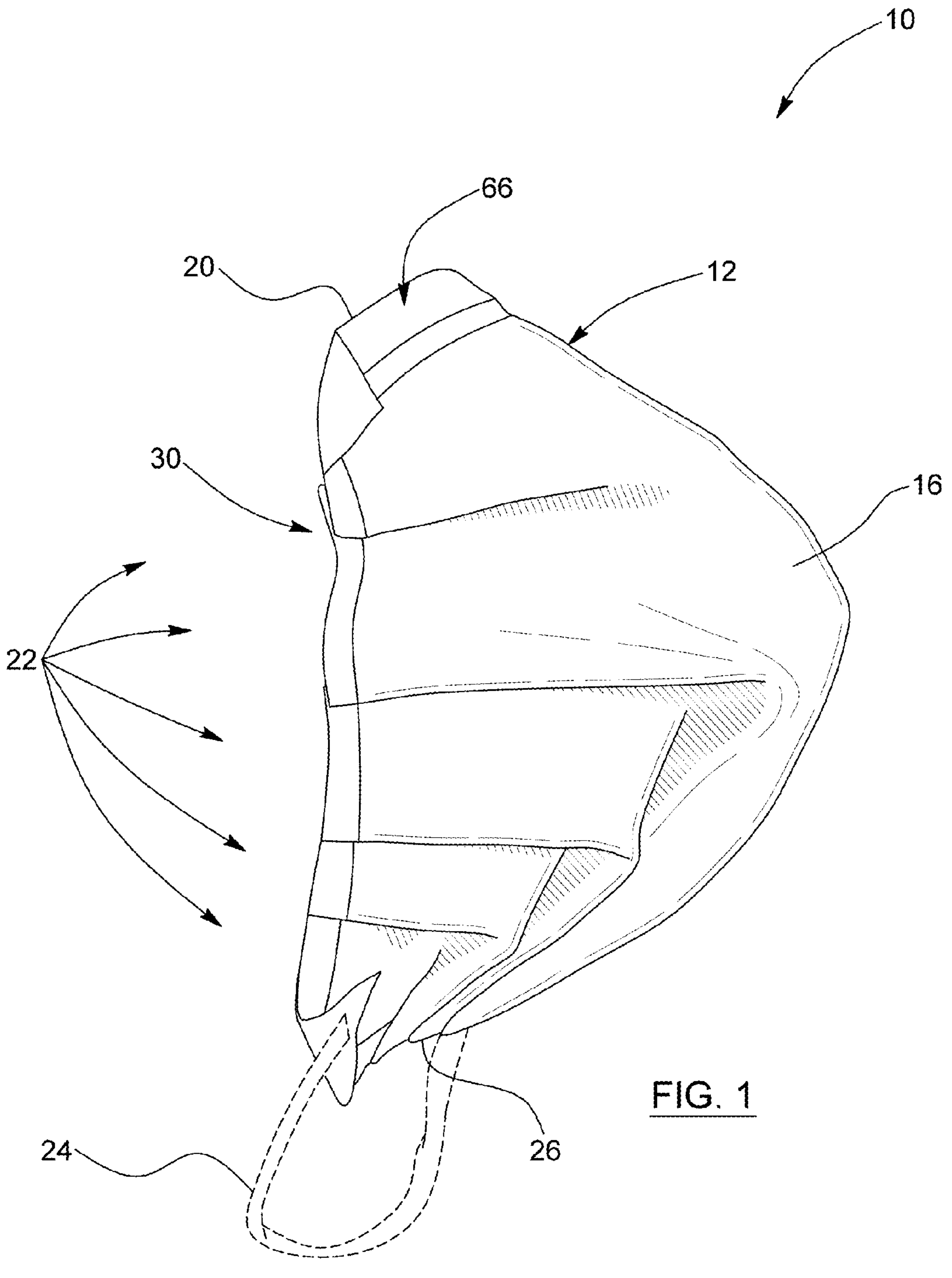
FIG. 1 is a Right side view of the Device of the presently disclosed embodiments

It will be understood that this disclosure presents illustrative embodiments by way of representation and not limitation. Numerous other modifications and embodiments can be devised by those skilled in the art which fall within the scope and spirit of the principles of the presently disclosed embodiments. In the following description, similar features in the drawings have been given similar reference numerals. In order to preserve clarity, certain elements may not be identified in some figures if they are identified in a previous figure.

DETAILED DESCRIPTION

An Ergonomic Protective Device, such as that described in the presently disclosed embodiments, will provide an optimum solution for a broad field of applications. In order to meet the criteria for ergonomic products and to comply with existing standards, this Ergonomic Protective Device combines lightweight and soft fabric materials, donning elastic loops, special design and positioning of three-dimensional V-shaped folds, and the use of welding techniques best used in high speed plastic bonding operations. The resulting product is an Ergonomic Protective Device that fits snugly to facial profiles with different surface anatomies and effectively entraps more than 99 percent of submicron particles and biological objects. Moreover, the wearer experiences significantly reduced air resistance at the same level of respiratory protection in comparison with existing models of facemasks and respirators.

Ergonomic protective air filtration devices and methods for manufacturing the same are disclosed herein. According to one aspect, there is provided an Ergonomic Protective Device, which is formed to fit comfortably over the lower half of the nose, the lips and mouth, the anterior part of the jaw, and the line behind the nasolabial sulcus of the wearer, comprising:

- an arrangement in which at least two layers of air permeable material are stacked together, the arrangement forming a body, a periphery, and a back;
- a plurality of three-dimensional V-shaped pleats extending from the arrangement's periphery into a convex structure that defines the device body, and
- a retaining means affixed to the body of the Device to secure the device to the face of the wearer and to create a breathing chamber defined by the back (inner) side of the device, the lower half of the nose, the lips and mouth, the anterior part of the jaw, and the line behind the nasolabial sulcus of the wearer.

According to another embodiment, there is provided an Ergonomic Protective Device as defined hereinabove, wherein the periphery of the device includes a bottom edge, a right side edge and a left side edge wherein the bottom edge comprises a bottom right-side pleat located on the right side of the bottom edge and a bottom left-side pleat located on the left side of the bottom edge. The bottom right-side pleat interlocks with a corresponding pleat on the right side edge and the bottom left-side pleat interlocks with a corresponding pleat from the left side edge.

According to another embodiment, there is provided an Ergonomic Protective Device as defined hereinabove, wherein the device further comprises a second bottom left-side pleat and a second bottom right-side pleat, the second bottom right-side pleat interlocking with a corresponding second pleat on the right side edge and the second bottom left-side pleat interlocking with a corresponding second pleat from the left side edge. The device may comprise still more sets of interlocking three-dimensional V-shaped pleats, or an array of pleats positioned on the device periphery arranged in the manner described above.

According to another embodiment, there is provided an Ergonomic Protective Device as defined hereinabove, wherein the interlocking bottom side pleats and side edge pleats form specific angles at their points of intersection.

According to another embodiment, there is provided an Ergonomic Protective Device as defined hereinabove, wherein the arrangement of stacked layers comprises an external layer made of a spunbond fabric, a filtering layer made of a meltblown fabric, and an internal layer made of a spunbond fabric, each of said fabrics being air permeable.

According to another embodiment, there is provided a method for constructing the Ergonomic Protective Device as defined herein, which fits comfortably over the lower half of the nose, the lips, the mouth, the anterior part of the jaw, and the line behind the nasolabial sulcus of the wearer. The method comprises the steps of:

a) prearranging of at least two layers into a precursor panel, where each layer is made of a permeable material, the arrangement forming a body, a periphery, and a back;

b) forming the Arrangement of layers by folding a plurality of three-dimensional V-shaped pleats extending from the Arrangement's periphery into a convex structure that defines the Device body, so that the back of the Device creates a Breathing Chamber adapted for covering the nose, lips and mouth, chin and portion of the cheeks of the wearer;

c) joining the layers of the Arrangement and said pleats at the periphery of the Device and at a plurality of specific points throughout the Arrangement of layers; and d) affixing the periphery of the Device with a means of retaining the Device to the face of the wearer, thereby creating a Breathing Chamber delimited by the back (inner) side of the Device, the lower half of the nose, the lips and mouth, the anterior part of the jaw, and the line behind the nasolabial sulcus of the wearer.

According to another embodiment, there is provided a method as defined hereinabove, wherein step c) of the method further comprises the sub-steps of:

i) folding a bottom pleat on the right side and folding a pleat on the right side such that the bottom right-side pleat interlocks with the pleat on the right side; and ii) folding a bottom pleat on the left side and folding a pleat on the left side such that the bottom pleat of the left side interlocks with the pleat on the left side.

The terms left, right, bottom and top should not be used to restrict the scope of the presently disclosed embodiments. These terms are meant to refer to the typical orientation of the Device when worn by a person. By "back of the Device," it is meant the back (inner) surface of the Device, which faces the nose, mouth, cheeks, and chin of the wearer.

According to another embodiment, there is provided a method for constructing the Ergonomic Protective Device as defined herein to provide specific protection against contaminated droplets, fluid splashes, solid particulates, pathogenic microorganisms, aerosoled air pollutions, or to prevent ignition of the Device materials, wherein:

either selected layers or all layers of the Device are treated with special agents during the fiber forming process or applied on the fabric surface to induce desired functional effects;

a bioactive agent or a combination of bioactive agents are applied to one layer or to selected layers of the Device in addition to surface tension modifiers, thus providing enhanced protection against detrimental microorganisms dispersed in droplets or aerosols;

either selected layers or all layers of the device are treated with low molecular weight polymeric materials during the fiber forming process or applied on the fabric surface to alternate or enhance the surface tension of the treated fabrics; or a flame retardant agent or combination of flame retardant agents are applied during the fiber forming process or impregnated into the fabric to either the first intake fabric layer or more layers of the Device to prevent inflammation by life sparks.

The presently disclosed device is a lightweight Ergonomic Protective Device which filters air inhaled by a wearer and provides less restrictive breathability, while also feeling comfortable to wear. Furthermore, such device does not interfere with the wearer's lips and nasal orifices, does not restrict facial articulations, and provides unrestricted downward vision. The device is also made of cost effective materials and can be manufactured at high throughput and in high volume.

Figure 2:
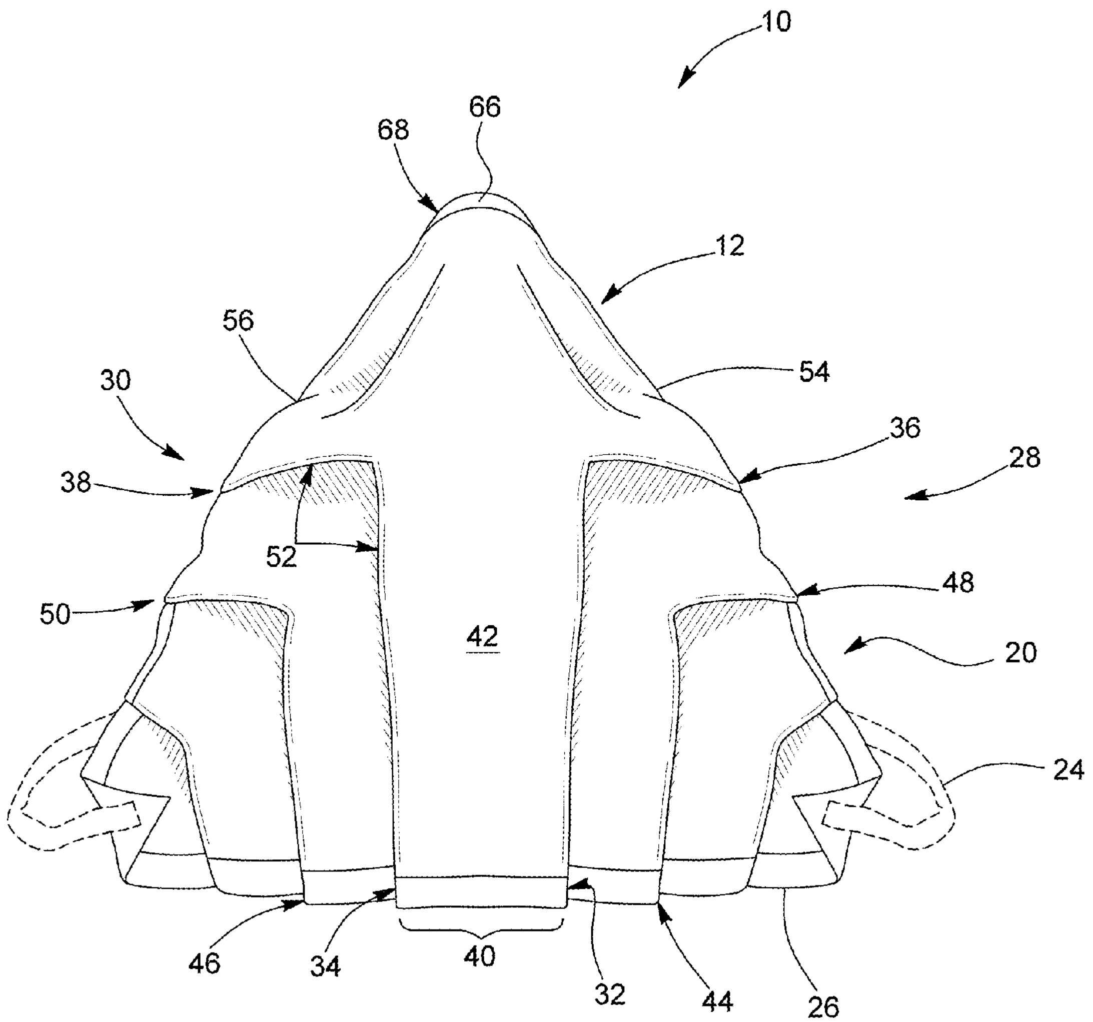
FIG. 2 is a Front view of the Device of FIG. 1
Figure 3:
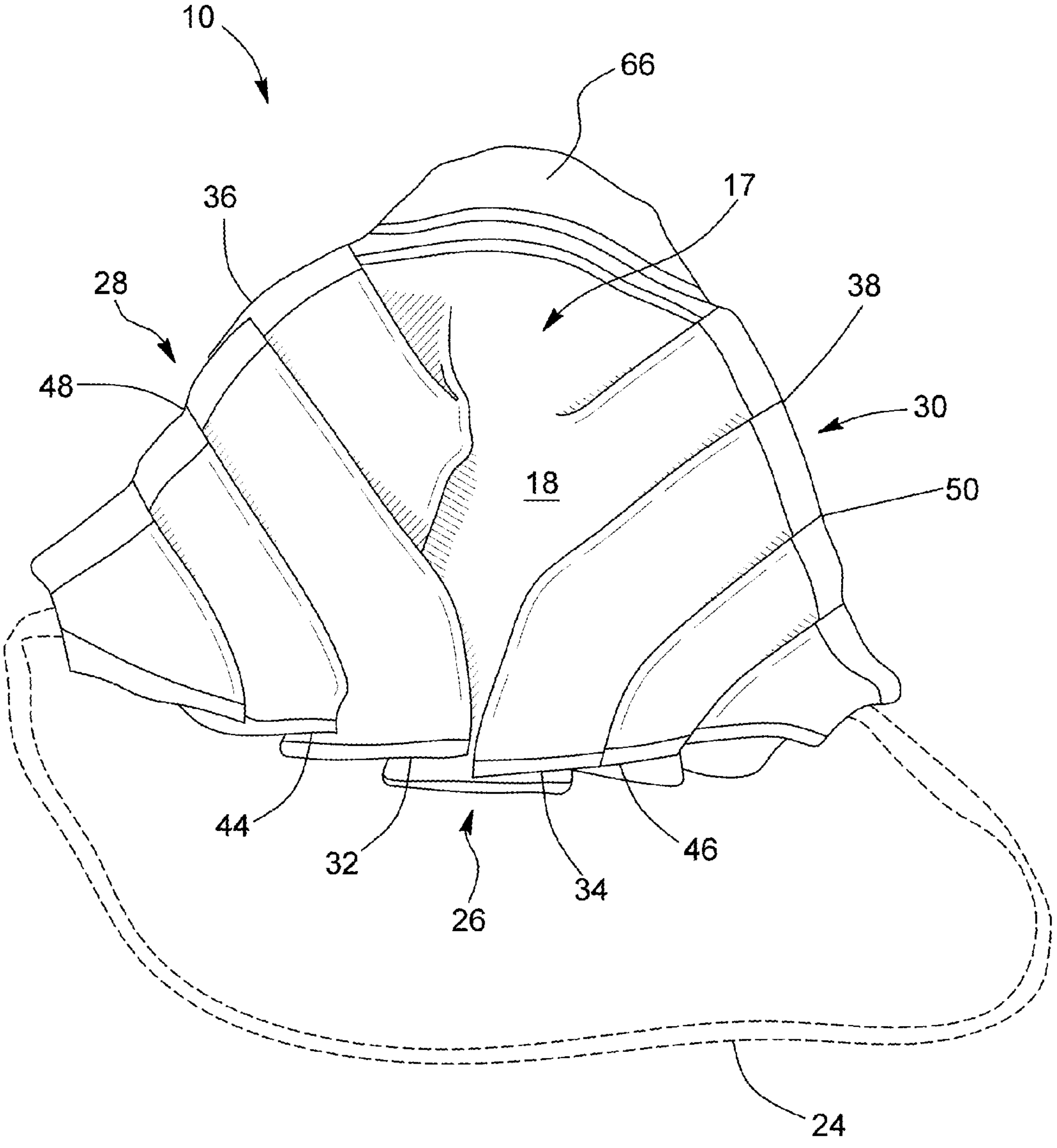
FIG. 3 is a Rear view of the Device of FIG. 1
Figure 4:
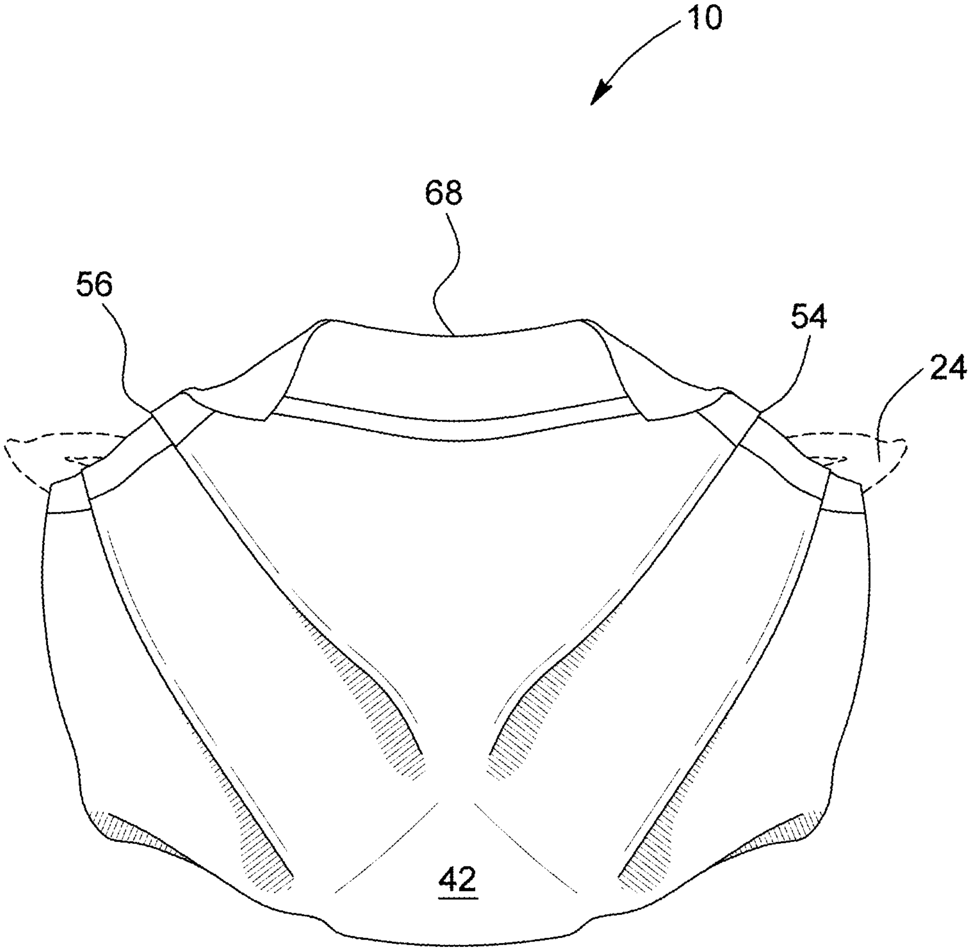
FIG. 4 is a Top view of the Device of FIG. 1
Figure 5:
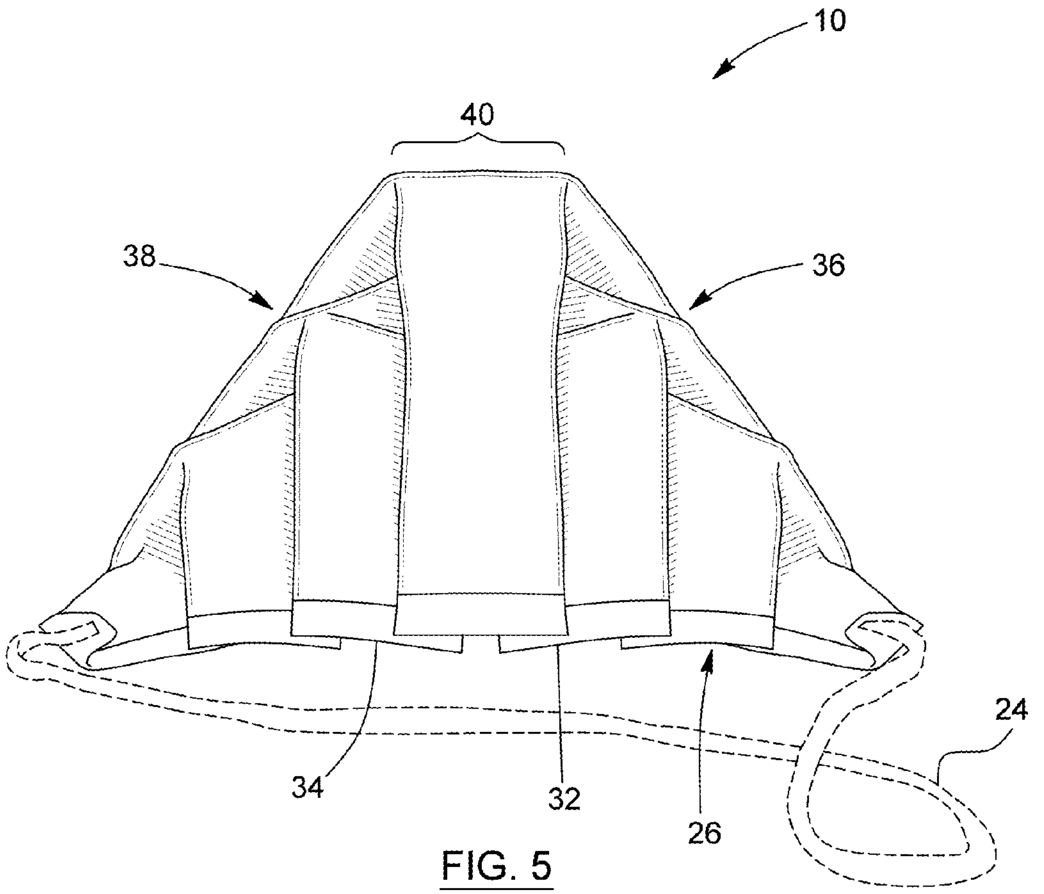
FIG. 5 is a Bottom view of the Device of FIG. 1
Figure 6:
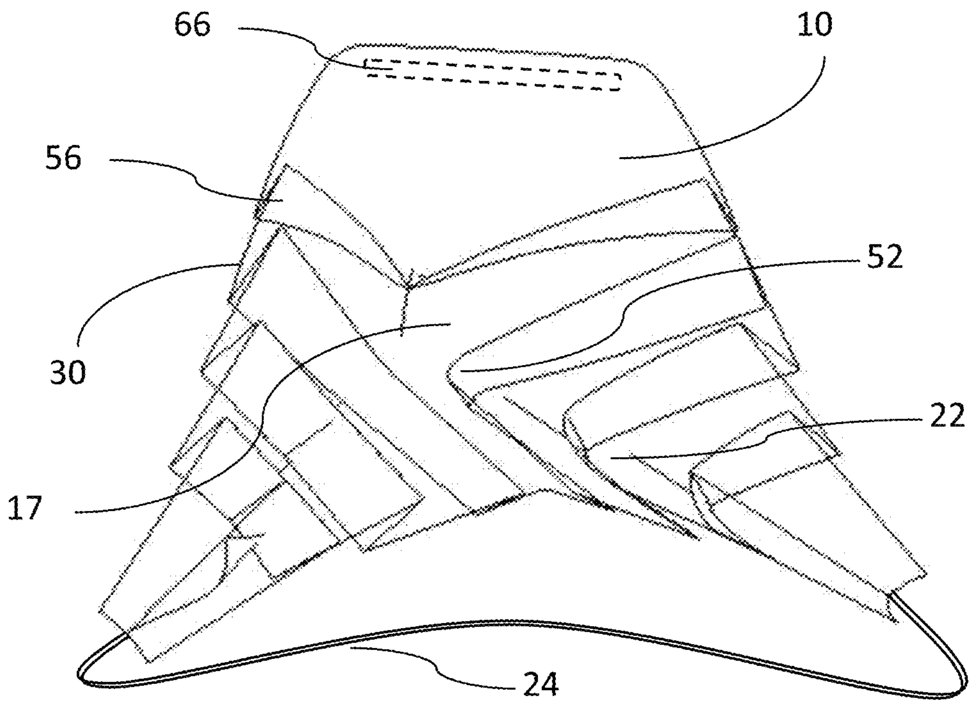
FIG. 6 is a Perspective Rear view of the Device of FIG. 1 showing the formation of three-dimensional V-shaped pleats

Referring to FIG. 1 to FIG. 6, FIG. 7A to FIG. 7C, and FIG. 9A to FIG. 9C, an Ergonomic Protective Device 10 is shown. The device 10 is formed to fit over the lower half of the nose, the lips, the mouth, the anterior part of the jaw, and the line behind the nasolabial sulcus of the wearer. The Device 10 comprises an arrangement 12 of stacked layers 14, each layer (as shown in FIG. 8A to FIG. 8E) being made of a permeable material. The arrangement 12 has a body 16 provided with a back of the device 18 and a periphery 20 (as shown in FIG. 3). A plurality of three-dimensional V-shaped pleats 22 extends from the left, right and bottom sides of periphery 20 and interlock at specific positions of the device body 16 (as shown in FIG. 1, FIG. 2, and FIG. 5). The rear face of the three-dimensional V-shaped pleats 22, along with the remaining unfolded part of the arrangement 12, define a breathing chamber 17 which covers the lower half of the nose, the lips, the mouth, the anterior part of the jaw, and the line behind the nasolabial sulcus of the wearer (as shown in FIG. 6). The device also includes retaining means 24 affixed to the body 16 in order to secure the device 10 on the face of the wearer and to create a breathing chamber (as shown in FIG. 3). When wearing the device 10, the breathing chamber is defined by at least a portion of the back of the device and by the lower half of the nose, the lips, the mouth, the anterior part of the jaw, and the line behind the nasolabial sulcus of the wearer.

The layers 14 of the arrangement 12 may have a trapezoidal, triangular or rectangular shape prior to being folded into three-dimensional structure characterized by the three-dimensional V-shaped pleats. In a preferred embodiment, a trapezoidal shape of the precursor panel is employed, as shown in FIG. 8A to FIG. 8E and FIG. 10.

The periphery 20 of the device 10 includes a bottom edge 26, a right side edge 28 and a left side edge 30 (as shown in FIG. 2). In an embodiment, the bottom edge 26 comprises a bottom right-side pleat 32 located on a right side of the bottom edge and a bottom left-side pleat 34 located on a left-side of the bottom edge. The bottom right-side pleat 32 and the bottom left-side pleat 34 each form a three-dimensional V-shaped pleat folded inward on the back of the Device, towards a central portion of the Device. The bottom right-side pleat 32 interlocks with a corresponding pleat 36 on the right side edge 28 and the bottom left-side pleat 34 interlocks with a corresponding pleat 38 on the left side edge 30. In a preferred, embodiment, the bottom right-side pleat 32 and the bottom left-side pleat 34 form a box pleat 40, the box pleat bulging out on the front facing side of the body 16 of the device 10 (as shown in FIG. 5). By box pleat, it is meant a flat double pleat made by folding the fabric under either side of the pleat.

The device 10 may further comprise a second bottom right-side pleat and a second bottom left-side pleat, the second bottom right-side pleat 44 interlocking with a corresponding second pleat 48 on the right side edge 28 and the second bottom left-side pleat 46 interlocking with a corresponding second pleat 50 from the left side edge 30. In a similar fashion, the device 10 may further comprise a third pair of bottom pleats interlocking with corresponding third pleats on the left and right sides of the device. In an embodiment, the bottom edge 26 can accommodate up to twelve pleats and the right side edge 28 and left side edge 30 can accommodate up to ten pleats each.

As shown in FIG. 2, FIG. 5 and FIG. 6, the bottom pleats 32, 34, 44, and 46 interlock with the side pleats 36, 38, 48, and 50 to form specific angles 52 at their respective points of intersection. These angles are formed by folding the fabrics in three-dimensional configuration where the angle varies from about 45 to 75 degrees. In a preferred embodiment, the angle formed by folding the fabrics in three-dimensional configuration is 60 degrees. In alternative folding patterns other than the three-dimensional V-shaped interlocking pleats design, these angles may range from about 30 to 120 degrees. These angles may improve the device functionality and formation of the breathing chamber with enlarged filtration surface. Moreover, these angles may also help ensure that the structural integrity of the device is maintained during the inhale-exhale cycles and prevent the device from collapsing over the wearer's mouth.

In an embodiment, the device further includes an upper right-side edge pleat 54 and an upper left-side edge pleat 56, in order to better accommodate the nose of the wearer.

Figure 8A:
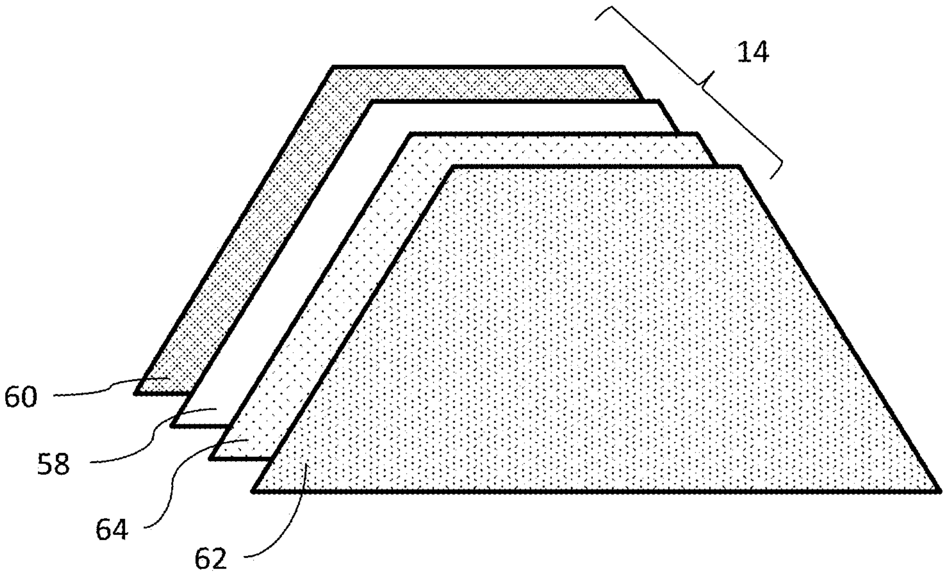
FIG. 8A is a schematic view of the construction of precursor panels and the arrangement of meltblown and spunbond fabrics to form an embodiment of the Ergonomic Protective Device for medical and healthcare applications.

Referring to FIG. 8A to FIG. 8E, in an embodiment, the arrangement 12 of layers 14 includes at least two layers of air permeable material made of nonwoven fabrics. The term "air permeable materials" as used herein refers to any porous or loosely structured materials that allow air to penetrate through the material without substantial resistance. In the case of personal air filtration devices, the air preferably flows through the filtration media at a relatively low pressure to ensure the necessary volume of air per each inhale-exhale cycle. In addition to specially made nonwoven fabrics, some loosely woven fabric materials and open porous foams may have suitable permeability. Typically, permeability is in direct correlation with the thickness of the material and is set in specific ranges according to industry standards. In the embodiment of FIG. 8A, devised for healthcare and medical applications, the Arrangement may include a filtering layer 58 made of a meltdown fabric and an internal layer 60 made of a spunbond fabric, each of these fabrics being air permeable. In some embodiments, the Arrangement further includes an external layer made of a spunbond fabric, which is also air permeable.

The weight of the spunbond fabric varies from about 7 to about 75 grams per square meter, with about 33, about 22, and about 20 grams per square meter being the preferred weight for the two front layers (air intake) and the back (mouth) layer, respectively. The weight of the meltdown fabric may vary from about 2 to about 150 grams per square, with 25 grams per square meter being the preferred weight for the meltdown fabric.

In some embodiments, the arrangement 12 of layers 14 is formed by a first, outer layer 62 that is fabricated and treated for contact with contaminated ambient air and is made of polypropylene. Adjacent to the outer layer 62 is a second layer 64, treated or untreated and also made of polypropylene. A third layer 58, designed to act as a filtering layer, is made of a meltdown fabric. Finally, a fourth layer 60, designed to be in contact with the face of the wearer, is made of polypropylene and polyethylene and may contain special additives for tailored fabric characteristics.

In an embodiment, the first, outer layer 62 is made of about 33 grams per square meter polypropylene fabric, the second layer 64 is made of about 22 grams per square meter polypropylene fabric, the third layer 58 is made of about 23 grams per square meter meltdown fabric, and the fourth layer 60 is made of about 22 grams per square meter polypropylene/polyethylene fabric.

Depending on the field of application where the device is to be worn, the number of layers 14 and their specific characteristics may be adapted. FIG. 8B to FIG. 8E show other examples of the layers 14 of the device 10, namely for clean room applications, for industrial or heavy duty applications where the device provides a high protection against dust and fine particulates, and for welding applications, where the front layers of the device can incorporate fire-resistant fabrics. Other variations in the number of layers 14, the type of material used for the layers 14, and the type of coating or impregnation applied to the layers 14 may also be considered.

More specifically, the construction of the device in FIG. 8A includes a specially nonwoven fabric used in the first outer layer 62, which can be treated with a fluid resistant agent. The next layer 64 is made of nonwoven fabric that may be untreated or treated with a surface modifier agent. This sequence of specially treated front layers results in a hydrophobic-hydrophilic type of barrier, which is effective in blocking splashes and entrapping aerosoled contaminants.

Figure 8B:
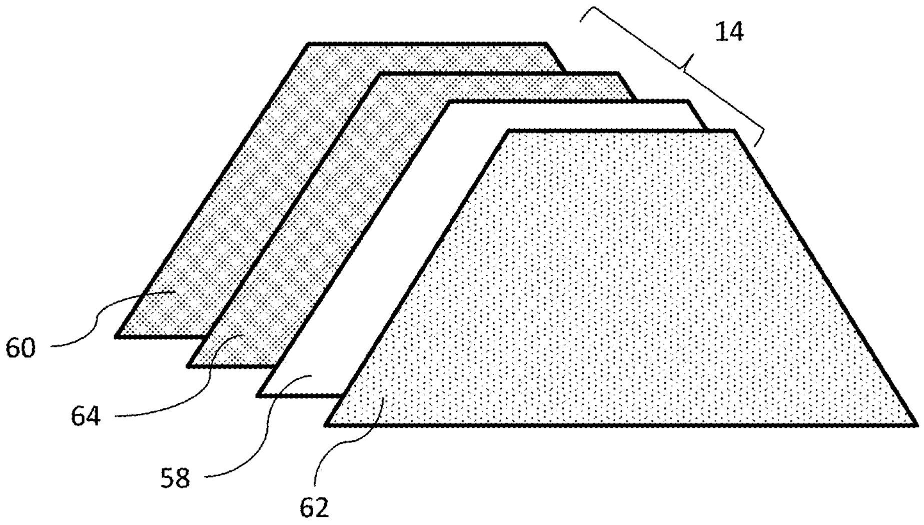
FIG. 8B is a schematic view of the construction of precursor panels and the arrangement of meltblown and spunbond fabrics to form an embodiment of the Ergonomic Protective Device for clean room applications.

In an embodiment, the device may entrap contaminants from the wearer's breathing, as shown in FIG. 8B. This is ideal when a working environment must be protected, as with clean rooms and electronics assembly sites. As illustrated in FIG. 8B, the inner side of the device is reinforced with a treated or untreated layer 64 (spunbond fabric) and layer 58 (meltblown fabric) which defuse and entrap aerosoled particles and microorganisms.

Figure 8C:
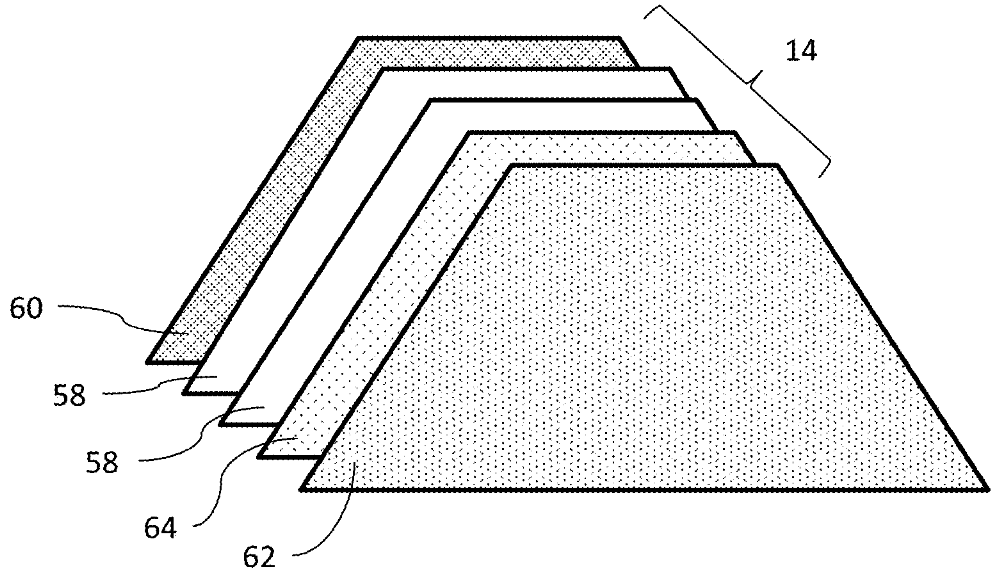
FIG. 8C is a schematic view of the construction of precursor panels and the arrangement of meltblown and spunbond fabrics to form an embodiment of the Ergonomic Protective Device for general industrial applications.

In an embodiment, the device may be constructed as a N-95 respirator and provide a high level of particulate protection, as shown in FIG. 8C. As illustrated in FIG. 8C, the body of the device is assembled with one spunbond layer 62, one treated or untreated layer 64, two layers of meltblown fabric that may contain special agents for enhanced entrapment of specific contaminants, and one layer 60 of soft spunbond fabric that provides comfort and reduces friction between the device and wearer's face.

Figure 8D:
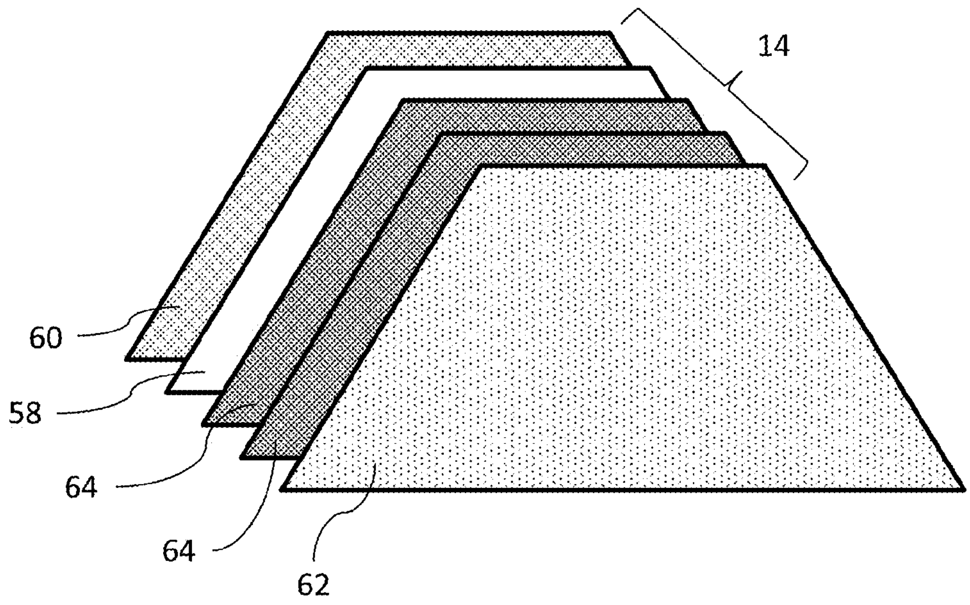
FIG. 8D is a schematic view of the construction of precursor panels and the arrangement of meltblown and spunbond fabrics to form an embodiment of the Ergonomic Protective Device for enhanced protection against pathogenic microorganisms (selected device layers being treated with bio-active agents).

In an embodiment, the device layers are treated with a bioactive agent for enhanced protection against pathogenic microorganisms, as shown in FIG. 8D. As illustrated in FIG. 8D, the layers 64 are treated with one or more agents to provide biocidal efficacy in addition to the mechanical entrapment of harmful bacteria and viruses. The device also may be constructed with special treatment of the meltblown layer 58. The inner layer is made of soft and flexible fabric 60 for comfort and a close facial seal.

Figure 8E:
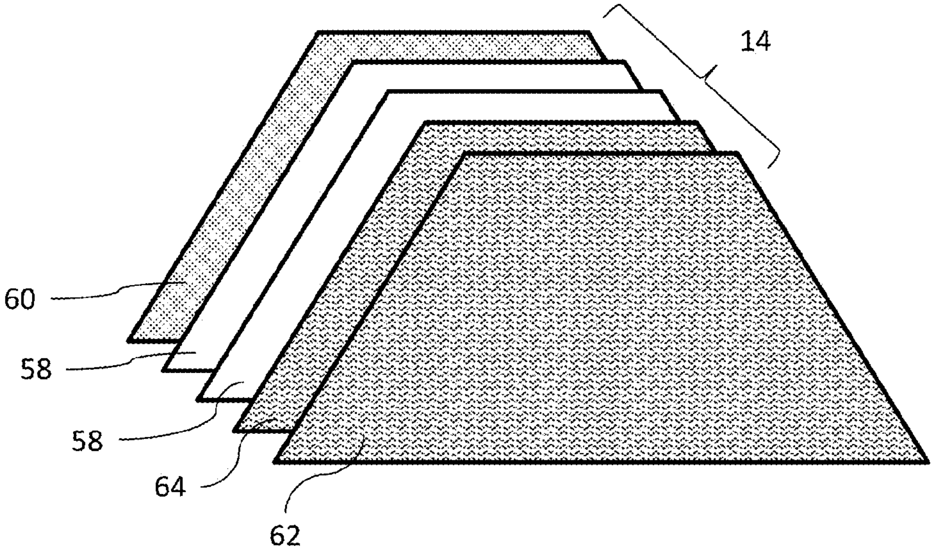
FIG. 8E is a schematic view of the construction of precursor panels and the arrangement of meltblown and spunbond fabrics to form an embodiment of the Ergonomic Protective Device for heavy duty industrial and welding applications (the outer layers of the device being welding spark-resistant).

In an embodiment, the device may be fire retardant, as shown in FIG. 8E. As illustrated in FIG. 8E, the device is comprised of layers 62 and 64 and may be assembled with two layers of special meltblown fabric 58 to meet the criteria for N-99 respirators.

The device may be used in different fields of application, such as in an operating room, general procedures, specialized healthcare, and dentistry. It may also be used in long-term and homecare facilities, as part of the general public bio-security safety measures, during pandemics and mitigation of respiratory infections. The Device can provide reliable protection for extended periods in any environment with elevated levels of particulates or aerosoled air contaminants, such as industrial plants, construction sites, and farming fields. The Device also may be worn for healthy precaution during mundane activities such as housekeeping or gardening.

According to the particular field of the application, either selected layers 14 or all of the fabric layers 14 may include special agents to induce a desired functional effect. A bioactive agent or combination of bioactive agents may be applied to one layer or to selected layers, thus providing enhanced protection against clinical pathogens or pandemic viruses. In an embodiment, the device is constructed with bioactive treated layers, as illustrated in FIG. 8D. Suitable bioactive agents include, but are not limited to, known in the art inorganic materials that can release metal ions at a controlled emission rate. Typical ions with proven biocidal activity are silver, copper, zinc or other metal ions, which are suitable for incorporation in specific polymer fiber, such as polyolefines. Exemplary inorganic bioactive agents include, but are not limited to, silver-zinc-glass compound, silver-zirconium-phosphate compound, silver-copper-zeolite compound, or nano-silver compounds, nano-copper compounds and nano-chromium compounds. Most commonly, these materials are ceramic type inorganic compounds or inorganic compounds insoluble in water and capable to emit metal ions at a predictable rate. Other suitable antimicrobial agents are organic compounds, such as quaternary ammonium salts, silane quaternary ammonium compounds, or organo-silver compounds.

In general, at their effective concentration of use suitable bioactive agents have biocidal or biostaic effect on particular pathogenic microorganisms, but do not cause any health or other detrimental problems to humans.

The specific type of each fabric, its weight, density, and other specific properties can be adapted for each intended use. As such, in an embodiment, the Device has at least one layer that includes a functional agent. Examples of suitable functional agents include, but are not limited to, surface tension modifiers, such as non-ionic surfactants based on low molecular weight copolymers of polyolefines having amphiphilic structure. Effective surface modifiers include, but are not limited to, organic hydrophilic compounds having a composition of linear alkyl phosphate and polyorganosiloxane blocks, or amphiphilic block copolymers. By way of a non-limiting example, suitable functional agents can be prepared of low molecular weight branched and linear sulfopolyesters, or mixture of the sulfopolyestes with other organic hydrophilic compounds. An illustration of the device as constructed with surface tension modifier treated layers is presented in FIG. 8A, FIG. 8B, and FIG. 8D, where layer 64 is treated. Still, in some embodiments, at least one of the layers is provided with a bioactive agent and functional agent.

In order to improve comfort and to properly retain the device 10 on the wearer's face, the device 10 is further provided with a nose clip 66 located on an upper edge 68 of the periphery of the device 10 (as shown in FIG. 2). In an embodiment, the nose clip 66 is a flexible aluminum strip embedded in a top fold of the arrangement 12 of layers 14, but specialty plastic and other types of nose clips may also be used.

In an embodiment, the layers 14 of the arrangement 12 are bonded to one another at the periphery and at specific points throughout the arrangement of layers. The bond may consist, for example, of a double line formed by hot wire press, impulse sealer, high frequency (RF) welding, ultrasound welding (US), or other bonding technique which is advantageous for high speed plastic bonding operations.

Figure 7A:
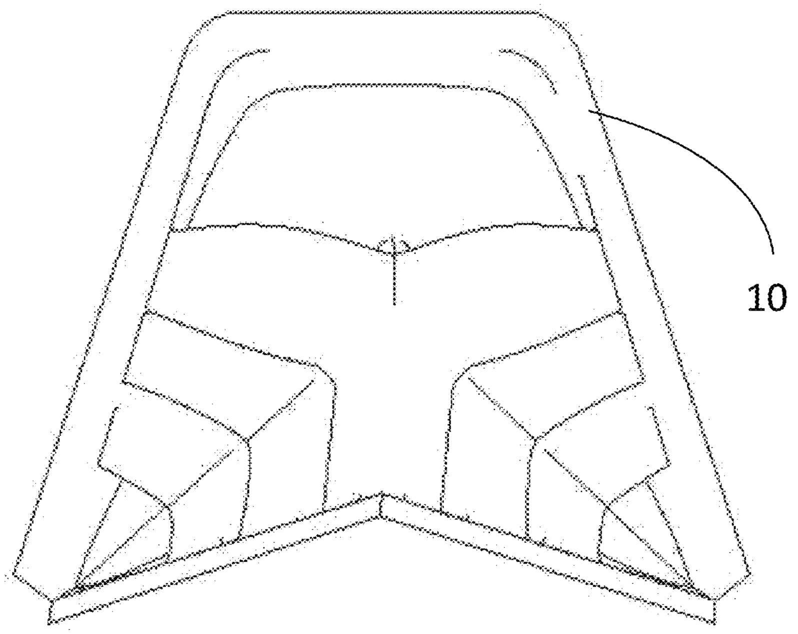
FIG. 7A is a Front view of the device in its finished assembly shape, according to the presently disclosed embodiments.
Figure 7B:
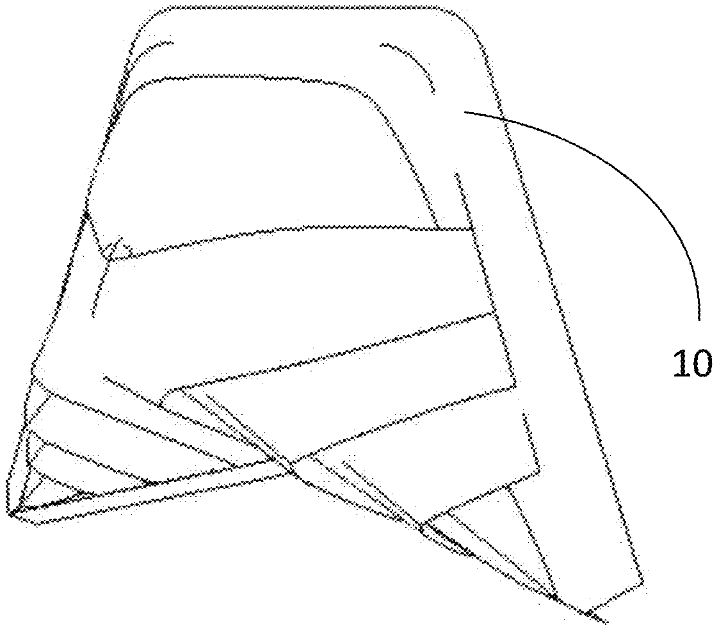
FIG. 7B is a Perspective view of the device in its finished assembly shape, according to the presently disclosed embodiments.
Figure 7C:
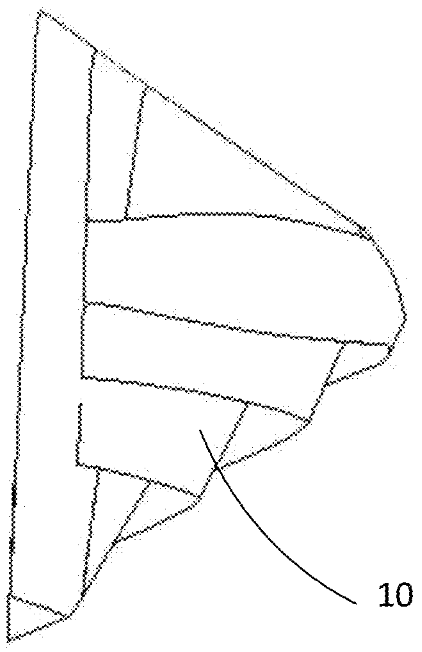
FIG. 7C is a Right side view of the device in its finished assembly shape, according to the presently disclosed embodiments.

As shown in FIG. 2, FIG. 5, and FIG. 7C, in some embodiments, the shape of the device 10 when viewed from the front is somewhat triangular with straight sides and bottom left and right halves. As shown in FIG. 6, FIG. 7A and FIG. 7B, in some embodiments, the shape of the device 10 is somewhat irregular when viewed from the right or left side.

FIG. 7A, FIG. 7B, and FIG. 7C illustrate the device in its finished assembly shape, and demonstrate the unique shape of the Device as it is produced on the special folding and welding fixture suitable for high-speed mass production. The dimensions of the precursor panels and the peripheral of the device are specially designed to form straight lines on the left and right edges and symmetrical V-shaped lines on the bottom edges. This design allows affixing in a one-step welding process all three-dimensional V-shaped pleats. Also, this particular design pattern allows the entire Device to be flat-folded for compact packaging.

Figure 9A:
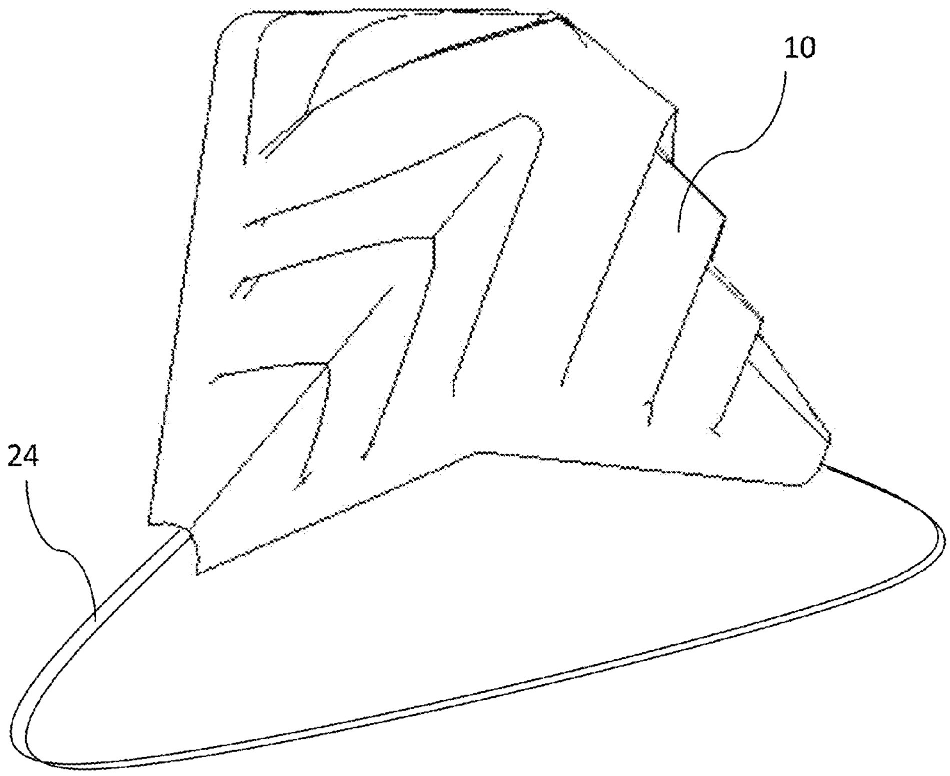
FIG. 9A demonstrates an example of a single neck loop donning option.
Figure 9B:
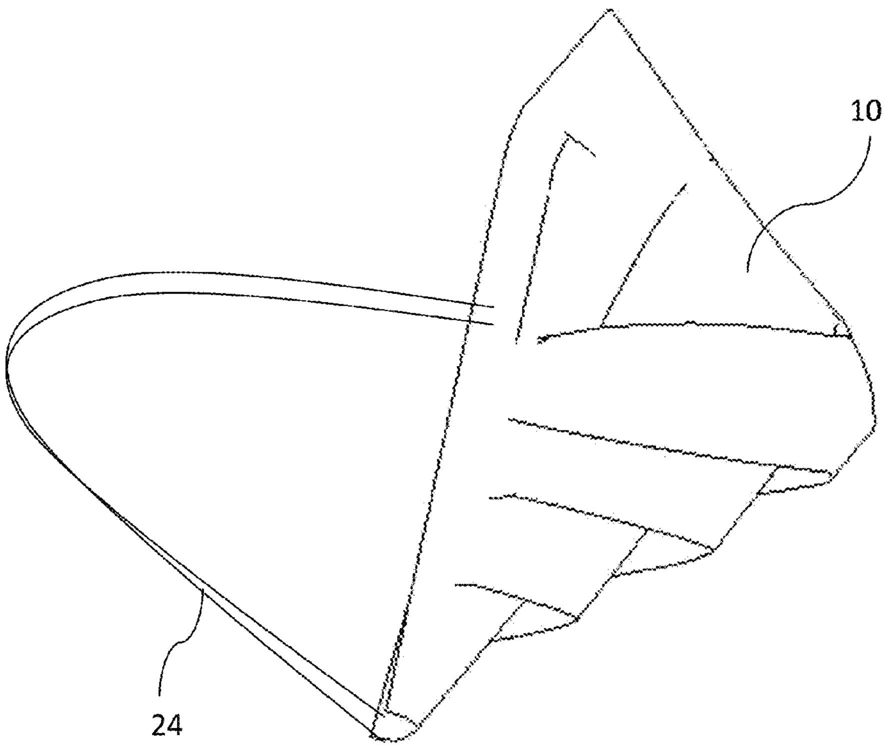
FIG. 9B demonstrates an example of a two earloops donning option.

Several types of retaining (donning) means 24 may be used for retaining the device 10 on the wearer's face. The retaining means may consist of a single neck loop, two neck loops, two ear loops, tie-on strings, an imbedded peripheral elastic string, or suitable combinations of different donning means. In an embodiment, the retaining means 24 comprises one or more elastic strips (as shown in FIGS. 9A and 9B).

In an embodiment, the retaining means 24 may consist of a single neck loop. To form a single neck loop, one end of the strip is affixed to a bottom right corner of the device, and another end of the strip is affixed to a bottom left corner of the device to form a loop around the wearer's neck (as shown in FIG. 9A).

In an embodiment, the retaining means 24 may consist of ear loops. To form ear loops, the retaining means 24 consists of two elastic strips, the first strip having one end affixed to a bottom right corner of the device and another end affixed to a right side of the top periphery corner, and the second strip having one end affixed to a bottom left corner of the device and another end affixed to a left side of the top periphery corner of the device (as shown in FIG. 9B).

Figure 9C:
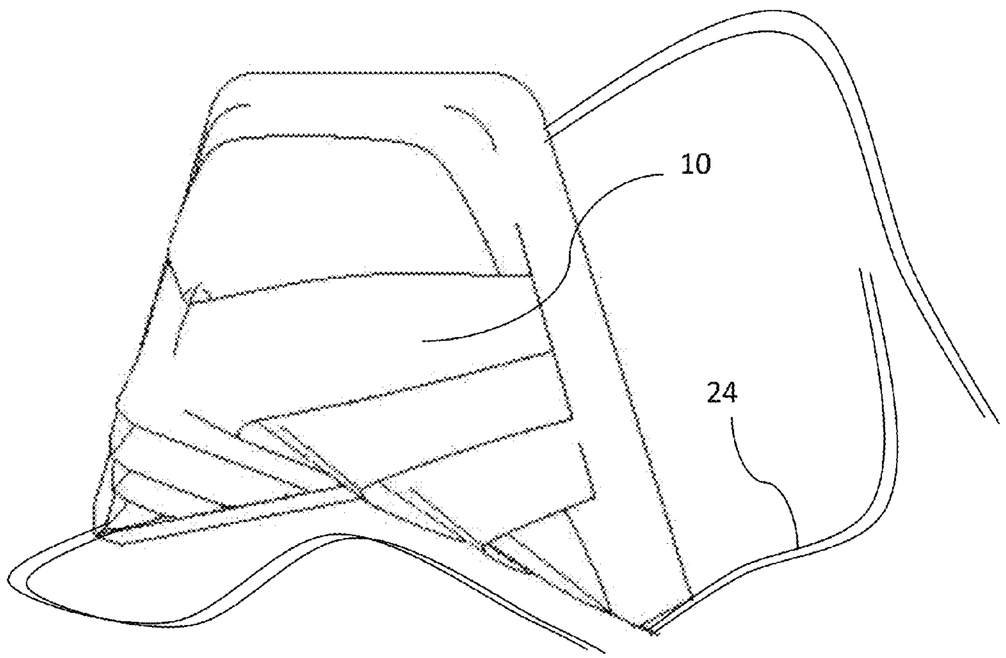
FIG. 9C demonstrates an example of a four tie-on strings donning option.

In an embodiment, the retaining means 24 may consist of four spunbond tie-on strips. To form four spunbound tie-on strips, each strip, 30 cm in length, is attached to one of the four corresponding corners of the top and bottom of the device (as shown in FIG. 9C).

In another embodiment of the device, the retaining means 24 is an elastic strip affixed and stretched around the right, bottom and left sides of the periphery of the device. In other words, the elastic strip circumvents the right, bottom and left side of the device and no loop is required (loop-free version) to hold the device in place. Thus, the combined actions of the circumvented elastic strip and the nose clip secure the device retention on the wearer's face.

Figure 10:
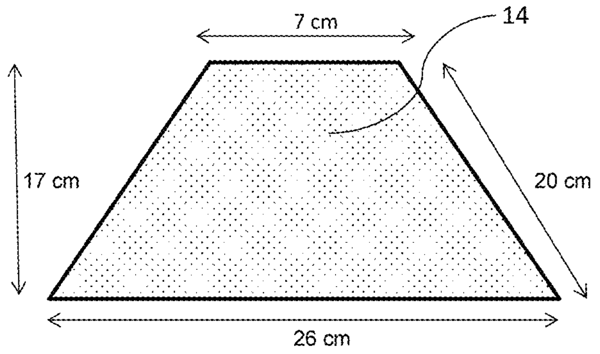
FIG. 10 demonstrates dimensions of layers of fabric for device sizes Small (S), Medium (M), and Large (L).
Figure 10:
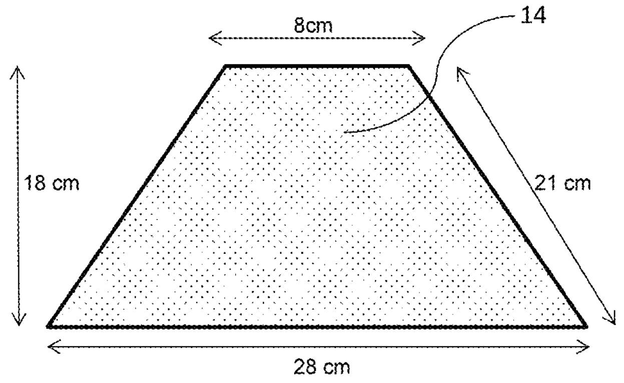
Figure 10:
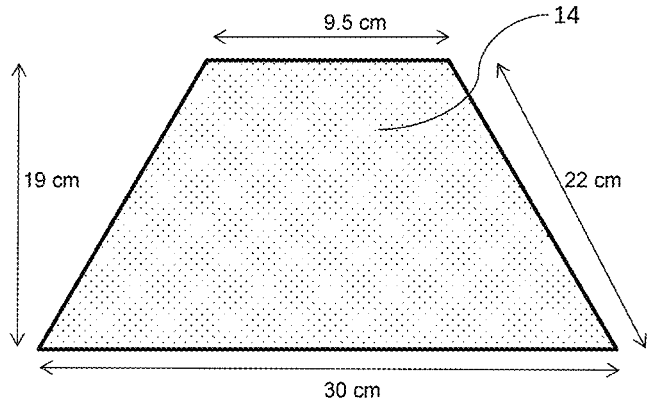

In an embodiment, a medium size of one version of the Device can be constructed as follows: all four layers of fabric are pre-cut into panel precursors, in the shape of a trapezoid with a base edge length of 28 cm, a top edge length of 8 cm, side edge lengths of 21 cm and a height of 18.5 cm. Other sizes, such as small and large sizes, can be cut in proportional dimensions, as shown in FIG. 10. To properly fit the Device over the wearer's face, a flexible aluminum strip, preferably about 5.5 cm long by about 0.3 cm wide, is embedded in a top fold of the panel precursor. Each side of the Device contains four pleats, each pleat being 1 cm in depth. The shape of the Device under the chin is formed by one double fold centered in the middle of the bottom edge, the pleats being approximately 1.0 cm in depth. The bottom edge includes two more pleats on each left and right side of the bottom edge, the pleats having a depth of about 1 cm. The first neck loop is connected to the bottom corners of the Device by folding in the corners, thus creating a 2 cm×2 cm reinforced triangular piece at the intersection of the nasolabial sulcus and the mandible. The second neck loop is connected to the upper side folds near the inclusion of the nose piece.

There is also provided a method for constructing the device described above. The first step of the method, step a), comprises prearranging the layers, each layer 14 being made of a permeable material, in order to form a body. The body 16 of the arrangement 12 includes a back of the device 18 and a periphery 20. The second step of the method, step b), comprises forming a plurality of pleats 22, which extend from the left, right and bottom sides of periphery 20 and interlock at specific positions of the device body 16 (as shown in FIG. 2 and FIG. 5). Once the pleats 22 are formed, the back of the device 18 defines a breathing chamber that covers the nose, mouth, chin and portion of the cheeks of the wearer. A third step, step c), comprises joining the pleats 22 and the unfolded part of the layers 14 of the arrangement 12 at the periphery 20 of the device 10. Finally, in step d), retaining means 24 are affixed at the periphery of the device 10 in order to retain the device to the face of the wearer, thereby creating a breathing chamber defined by the back of the device and lower half of the nose, lips and mouth, the anterior part of the jaw, and the line behind the nasolabial sulcus of the wearer.

In an embodiment, step c) comprises the sub-steps of i) folding a bottom pleat 34 on the right side and folding a pleat 38 on the right side such that the bottom right-side pleat 34 interlocks with the pleat 38 on the right side; and ii) folding a bottom pleat 32 on the left side and folding a pleat 36 on the left side such that the bottom left-side pleat 32 interlocks with the pleat 36 on the left side.

Figure 11:
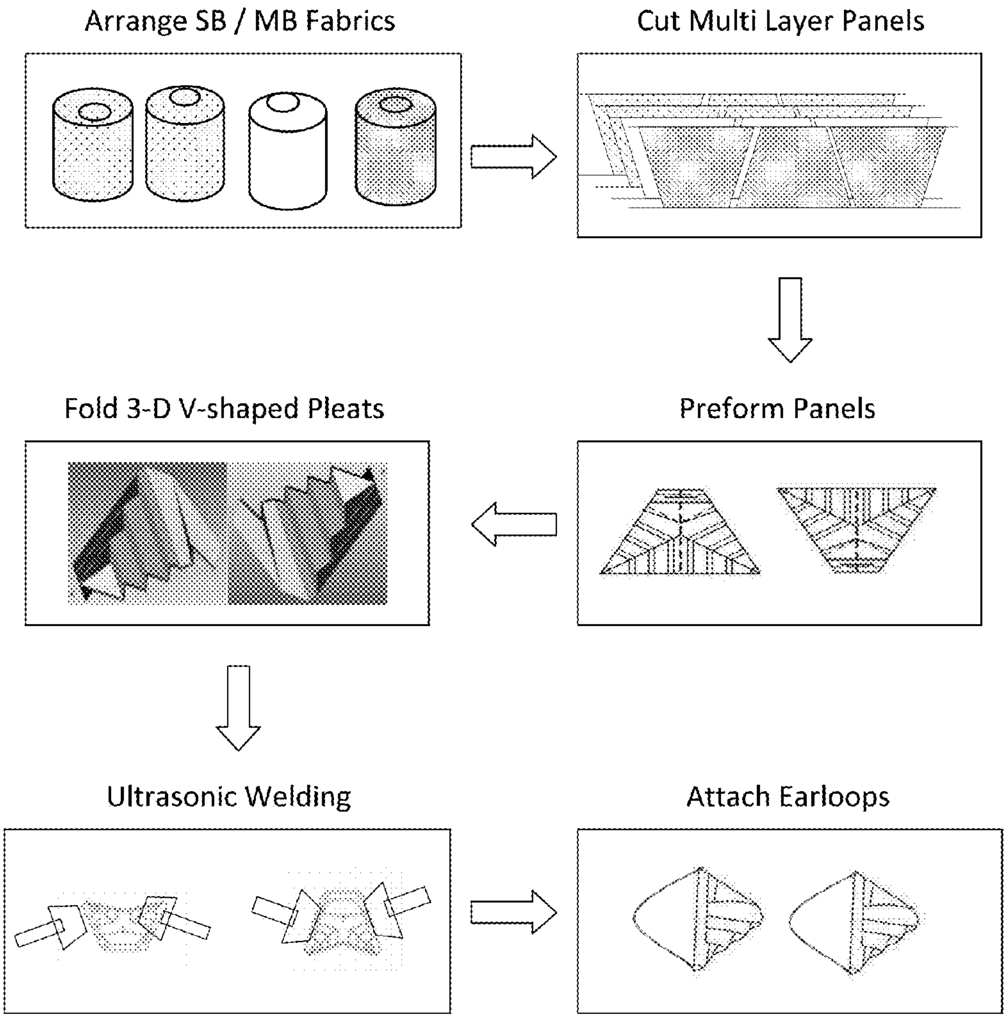
FIG. 11 is a Schematic of Multi-Module Device Assembly Line.

In an embodiment, the device 10 is designed for mass production, as shown in FIG. 11, and is constructed from pre-cut flat arrangement 12 (or panel precursor) of spunbond and meltblown fabrics. In an embodiment, the first, outer layer 62 (air intake) is made of one piece of 33 grams per square meter (gsm) PP spunbond fabric (SAL-33G). The second layer 64 is made of one piece of 22 gsm PP spunbond fabric (SAL-22G). Next, the filtration layer 58, or third layer, consists of a layer of 23 gsm meltblown fabric (SAL-23M). Finally, the fourth layer 60 consists of one piece of 22 gsm spunbond bi-component PP-PE fabric (SAL-22H), this layer being in direct contact with the facial skin of the wearer.

Example 1

In an embodiment, the device can be manually constructed as described below.

Prearranging the Layers

Four fabrics are unrolled in a specific orientation, to match the "face" or "back" side of the nonwoven fabrics according to the design specification. A trapezoidal precursor panel is cut to predetermined dimensions by positioning the cutting device at a specific angle. When this procedure is automated, some or all of the panels may be cut sequentially in order to reduce waste of fabric (as shown in FIG. 11).

Construction the Top Side

Each side of the precursor panel, or arrangement of layers, is partially laminated by bonding the layers to one another at the periphery 20 and at specific points throughout the arrangement of layers, such as by using a hot strip impulse sealer, by double lines, such lines being approximately 0.5 cm apart. The nose clip 66 is then positioned inside a 1 cm fold formed at the top of the trapezoidal panel. In an embodiment, the nose clip 66 may be an aluminum strip. The edge of the fold is sealed across using hot wire press, impulse sealer, high frequency (RF) welding, ultrasound welding, or other bonding technique advantageous for high speed plastic bonding operations. Under this seal line, a second line is also marked using impulse sealer, about 0.5 cm away form the first line, in order to form a dual seal. Next, the top two corners of the trapezoid, in the shape of a 1.5×1.5 cm triangle, are folded forward and sealed to the front of the device 10 to create reinforcement points for attachment of the donning means 24.

Construction of Pleats on the Bottom Edge

Two pleats of 1.0 cm in depth are formed in each direction from the center of the bottom edge 26. This creates a central double fold, which is secured by spot welding of the edges. In an automated version of this procedure, the welding is achieved using radiofrequencies (also known as the RF technique). Two additional pleats of 1.0 cm in depth are formed on each side of the central double fold. On the right side of the bottom edge, the first additional pleat is located approximately 1 cm from the central-right fold, and the second additional pleat is located approximately 1.5 cm away from the first right additional fold. The left pleats are formed in a similar fashion.

Construction of Left and Right Side Pleats

A right-side pleat, located about 3 cm from the top corner of the device and approximately 1 cm in depth, is formed and spot sealed. A second right-side pleat 1 cm in depth is formed 2.5 cm away from the first right-side pleat and spot sealed. This second side pleat intersects in the middle portion of the device body with the corresponding central fold formed at the bottom of the device. A third pleat of about 1 cm in depth is formed 2 cm away from the second right-side pleat and spot sealed. This third side pleat interlocks with the corresponding second fold formed on the bottom edge of the device. A fourth right-side pleat of about 1 cm in depth is formed 1 cm away from the third side pleat. This fourth side pleat interlocks with the corresponding third pleat formed on the bottom edge of the device. The combined pleat formation creates a stepped pyramidal shape. The left side pleats are assembled in symmetrical fashion. In an automated version of the method of assembly, both left and right sides are formed simultaneously.

Retaining Means

One of various retaining options may be attached to the device to fit particular applications or customer preferences. To affix a neck loop, the bottom corners of the device are folded outward to form two 2 cm×2 cm triangles and spot heat sealed. An elastic strip about 26 cm in length is heat sealed and attached near the middle of the triangles. A top neck loop is added by folding the top corners of the device outward to form two 1.5 cm×1.5 cm triangles, spot heat sealing the top corners in place, and affixing an elastic strip about 30 cm in length near the middle of the top triangles by a heat seal or ultrasonic welding technique.

Due to the inherent close fit of the device to human faces with different superficial anatomy, the device may be securely attached to the face by means of a nose piece with specific stiffness and only one neck loop affixed to the bottom part of the Device, as shown in FIG. 9A.

In an embodiment, the retaining means 24 may comprise two ear loops, each ear loop including one end affixed to a bottom corner of the device and the other end attached to the folded edge formed by the top pleat of the device, as shown in FIG. 9B. This donning version is ideal for use by healthcare professionals who have to replace the device on a periodic basis.

In an embodiment, the device may be made with four spunbond tie-on strips, each about 30 cm in length, attached to the four corresponding corners of the top and bottom of the device, as shown in FIG. 9C. This particular donning version is mandated for all surgical masks used in the operating room because it provides the most secured fit of mask and prevents donning failure. FIG. 9C illustrates a donning means in compliance with the established sterile procedures for surgical operations.

In an embodiment, as shown in FIG. 8D, the device may consist of an ergonomic surgical mask devised to provide protection against airborne microorganisms. The ergonomic surgical mask is constructed of nonwoven fabrics treated with a predetermined proportion of bioactive agents. In an embodiment, layers SB2 and SB3 or all layers, both the inner and outer cover layers, and the inner filter media layer, may contain a composition of multifunctional biostatic agents integrated in the nonwoven fabrics. This bioactive composition is concentrated on the fiber surface and characterized by quick delivery of the active components during normal use of the device. Typically, fabrics treated with such composition not only entrap but also effectively deactivate pathogenic microorganisms in the passing air. The combination of the device design, filtration media and natural fabric feel provides comfort and normal breathing for extended periods while preventing cross-contamination of detrimental microorganisms between the wearer and the surrounding environment.

As illustrated in FIG. 8A to FIG. 8E and FIG. 10, in order to assemble the ergonomic surgical mask, prearranged layers of spunbond fabric (SBF) and meltblown fabric (MBF) are die cut to design patterns while the construction in layer sequence and type of fabric is governed by the intended use and desired product performance. The proper length and type of material for the nosepiece ensure close facial fit and prevent fogging of safety glasses in a typical indoor environment.

Example 2

High Throughput Assembly Method

In this example, the ergonomic surgical mask is produced on automated workstations where all fabrics are fed continuously in a prearranged pattern, the swatches are cut, a nosepiece strip is automatically folded into the top of the precursor and covered with spunbond fabric. Both top and bottom corners are folded in a triangular pattern and welded with an ultrasonic technique. Next, the three-dimensional V-shaped pleats are formed in a one-step folding process and secured simultaneously on both the sides and bottom of the device periphery with an ultrasonic welding technique. Two earloops are attached from an automatic feed, cut to a set length and welded with an ultrasonic technique at the corners of the mask. A schematic of the Multi-Module Device Assembly Line is illustrated in FIG. 11.

More specifically, the high speed automated mode of assembly consists of arranging the selected rolls of nonwoven fabrics according to the specific product design. These fabrics are fed to the first assembly module as a continuous multilayer strip precut to the desired mask size, as illustrated in FIG. 10. At this module, the fabrics are partially laminated at a plurality of locations throughout the trapezoid shaped precursor panels, separated from the feeding strip by a cutting device and transferred to the next module. On this module, the nosepiece is installed, the precursor panels are marked at the folding lines, partially folded in a simple convex formation, and forwarded to the next module. This folding module employs a high-speed mini-robotic system to create the three-dimensional V-shaped pleats simultaneously on the bottom, left and right sides. At the next module, the pre-folded parts are welded at the device periphery with a system of multiple ultrasonic welding heads. The finished parts, illustrated in FIG. 7A to FIG. 7C, are sent to the next module where the device donning strings are attached. At this stage the device is ready for multiple or single form packaging. This process is schematically illustrated in FIG. 11 and can be applied to a single or multiple parts assembly mode.

In an embodiment, the device materials for medical and healthcare applications have the following specifications:

Meltblown Fabric

MBF2508 made with Prospector MF650X PP resin, Basell

| | | |
|---|---|---|
| Basis Weight | g/m$^2$ | 23.0 |
| Thickness | mils | 6.9 |
| Airflow Resistance | ‘mm $H_2O$ @ 32 lpm; 100 cm$^2$ | 2.2 |
| NaCl Penetration | % @ 32 lpm; 100 cm$^2$ | 1.8 |

Spunbond Fabric

SBF22B40; core—35 MFR PP resin, Basell medical grade PH 835; sheath 60 MFR PP Metocene grade MF640T

| | | |
|---|---|---|
| Fiber construction | Bico | 60/40 |
| Basis Weight | g/m$^2$ | 22.0 |
| Thickness | mm | 0.2 |
| Fiber denier | dpf | 1.8 |
| Color | RJB | 79-189-229 |
| Airflow Permeability | cfm | 625 |
| CDE@Peak | % | 125 |
| CDT@Peak | N | 40 |
| MDE@Peak | % | 100 |
| MDT@Peak | N | 60 |

Spunbond Fabric

SBF20B50; core—35 MFR PP resin, Basell medical grade PH 835; sheath 27 MFR PE resin, grade ACP 7740F3

Nosepiece 5.5 cm×0.3 cm, A1 allow—grade & performance specs selected by customer Neck-Loops/Ear-Loops 30 and 26 cm, knitted elastic strips—grade & performance specs selected by customer, Option Earloops—21 cm, knitted elastic strips All product characteristics and material specifications indicated above are provided as examples only. In an embodiment, pleats of different depths and locations may be formed.

Besides the ergonomic fit and compacted design, the device is comfortable to wear, even when worn for an extended period in hot and humid environments subjected to air-born contaminants. The selection of fabric materials ensures comfort and breathability, reduces restrictions on inhaled air, and does not restrict mouth articulation. The device aims to reduce the constraints imposed to facial muscle movement while speaking without compromising the seal of the device over the wearer’s face.

Another advantage of the device resides in its shape, which minimizes unnecessary coverage of the face with electrostatic manmade fabric, thus reducing air temperature within the breathing chamber. While wearing the device, the wearer has a larger portion of his cheeks exposed to ambient air, which allows for natural cooling of the face.

In addition, the shape and folding of the pleats of the device provide the wearer with improved downward vision, which is especially important for professionals requiring precise hand-eye coordination. Several donning options are possible: one neck loop for safe removal and reuse when appropriate, two neck loops for more permanent and secured wear, two ear loops for ease of donning and frequent replacement, or a circumvented elastic string (the loop-free version).

In an embodiment, the device may be reusable or designed for single use.

Ergonomic Device Breathing Chamber and Surface to Volume Ratio

Several popular shapes of disposable respirators are recommended by authorities in North America and Europe for respiratory protection, namely Duckbill, Box-4 panel shape, and the traditional Cup-shape. These respirators are typically constructed with one or more rigid nonwoven fabrics to retain the relatively simple convex shape that forms the breathing chamber. However, these simple and pre-formed geometric shapes do not fit well over the complex topography of the human face. When placed over the wearer’s face, these types of facemasks tend to cover a significant portion of the chin and under the chin areas. As a result, the effective breathing chamber is reduced from the original total volume measured by the geometric dimensions of the specific respirator. More importantly, a significant portion of the total surface of these respirators is in close contact with facial skin, which results in diminished effective surface for passing the inhaled and exhaled air. The effective surface is the actual surface of the breathing chamber as defined by the space between the specific facial topography and the inner concaved surface of the respirator. This interrelationship between the facemask geometry and the effective surface is more prominent in the case of standard surgical masks where the breathing chamber is more often determined by the geometric dimensions of the wearer's nose.

The fundamental deficiency of common facemasks and respirators is resolved with the design and construction of the Ergonomic Protective Device. In contrast to the simple geometric shapes of standard protective masks, the device incorporates numerous three-dimensional V-shape pleats that allow for significant increase in effective surface while maintaining the compacted volume of the breathing chamber. In Table 1 below, the volume and surface characteristics of the ergonomic device of the presently disclosed embodiments is compared with the following common respirator masks: duckbill, box, and cup-shape, referenced as S-5DZR, G2130, and M8210 in Table 1, respectively. All measurements are conducted on a mannequin with a transparent head to observe proper fit and ensure precision in data collection.

To define common criteria for optimum effective surface and compacted breathing chamber volume, the different types of protective face masks are compared based on the Surface to Volume Ratio (SVR). A higher SVR number benefits breathability due to larger effective surface and reduced breathing chamber volume. The test data summarized in Table 1 demonstrate that the popular respirators are characterized by an SVR value of below 1, while the presently disclosed device is more than twice as effective with an SVR value of 2. This difference in SVR numbers is in concurrence with the lower air resistance data for the Ergonomic Device, Delta P, EAR, IAR, as shown in Table 2. This exceptional filtration efficiency at specific level of protection and media design is in direct correlation with the inventive design of multiple three-dimensional V-shaped pleats characteristic for the Ergonomic Protective Device. The Ergonomic Protective Device will also allow people and children with difficulties or inabilities to breathe through restrictive filtration devices to have an economic, safe and reliable protective facemask. In addition, the Ergonomic Protective Device provides the best effective surface of the breathing chamber per total weight of the device in comparison with the traditional shapes of facemasks as exemplified by the STW (Surface to Weight) ratio, as referenced in Table 1.

Acceptable SVR values of 1 to 4, and more preferably SVR values of 2, will be used in the design of various SCB (Superior Comfort & Breathability) and ESR (Ergonomic Safety Respirator) Devices to provide the desired level of protection and reduction in air resistance. Practically, SVR values of 3 can be achieved by proportional modification of the described method of assembly. Devices with higher SVR can be produced, however, some changes in the folding pattern may be necessary. In this case, a primary folding structure will have the three-dimensional V-shaped pleats, and a secondary folding structure will incorporate the primary pleats in pairs by welding the pleats edges at the device periphery.

TABLE 1

Surface to Volume Ratio (SVR) of Ergonomic Protective Device and Typical Shapes N-95 Respirators

| | | Variations N-95 Respirators | | |
|---|---|---|---|---|
| Device/Respirator ID | Ergonomic SCB 500 | Duck-bill S-5DZR | Box-shape G 2130 | Cup-shape M8210 |
| Total Surface, $sm^2$ | 265 | 234 | 225 | 160 |
| Total Volume, cc | 185 | 450 | 450 | 240 |
| Total Weight, g | 5.4 | 5.8 | 8.1 | 10.8 |
| Effective Surface/BC, sm2 | 235 | 115 | 133 | 66 |
| Volume/BC, cc | 115 | 150 | 160 | 70 |
| Surface to Volume Ratio SVR | 2.04 | 0.77 | 0.83 | 0.94 |
| Surface to Weight Ratio STW | 43.5 | 19.8 | 16.4 | 6.1 |

* Breathing Chamber (BC)

Private Data November 2011

Examples of Ergonomic (Hybrid Facemask-Respirator) Devices with Low Air Resistance and Enhanced Breathability The effect of low air resistance and enhanced breathability is directly related to the surface to volume ratio (SVR)—the multiple three-dimensional V-shaped pleats of the Ergonomic Protective Device provide increased surface for active air passage at the proportional consumption of permeable special fabrics. In general, the key air resistance criteria as Differential Pressure (Delta P) and Inhale and Exhale Air Resistance (IAR, EAR respectively) are almost 50 percent lower for the Ergonomic Protective Devices in comparison with the standard mask or respirators at specific level of protection. Table 1 above represents the actual values of the air resistance tests conducted with various Ergonomic Protective Devices of specific construction and the average numbers obtained from benchmarked products currently used in North America.

TABLE 2

Ergonomic Protective Device - Filtration Efficiency of SCB and ESR Hybrid Facemasks vs. Benchmark Masks & Respirators

| Performance Criteria | Test ID, units | SCB 300 | SCB 400 | ESR 400 | SCB 500 | ESR 500 | ZPM 700 | ESR 900 | BM1 HB/Mask | BM2 N-95 Respirator | BM3 N-99 Respirator |
|---|---|---|---|---|---|---|---|---|---|---|---|
| Differential Pressure | DP, mm | 2.2 | 2.5 | 2.5 | 2.8 | 4.4 | 3.0 | 6.0 | <5.0 | — | — |
| Inhalation Air Resistance | IAR, mm | 2.0 | 2.2 | 2.2 | 4.2 | 5.0 | 4.8 | 6.4 | 3.0 | 10.0 | 14.0 |
| Exhalation Air Resistance | EAR, mm | 1.0 | 1.4 | 1.6 | 4.8 | 5.4 | 5.2 | 6.8 | 2.0 | 12.0 | 16.0 |
| Particulate Filtration Efficiency | PFE, % | 97.5 | 99.5 | 99.5 | 99.6 | 99.8 | 99.9 | 99.9 | >95 | >97 | >99.9 |
| Bacterial Filtration Efficiency | BFE, % | 96.50 | 99.50 | 99.50 | 99.95 | 99.90 | 99.98 | 99.99 | >95 | — | — |
| Viral Filtration Efficiency | VFE, % | 96.50 | 99.50 | 99.50 | 99.95 | 99.90 | 99.97 | 99.99 | — | — | — |
| Sodium Chloride, non-oil | SCP, % | — | 95.0 | 95.0 | 97.0 | 97.0 | 98.0 | 99.9 | — | >97.0 | >99.5 |
| Synthetic Blood Resistance | SBR, mm | 120 | 160 | 160 | 160 | — | 160 | — | 160 | — | — |
| Product Total Weight, g | WT, g | 3.3 | 3.8 | 4.4 | 5.2 | 5.4 | 5.4 | 5.8 | 3.6 | 10.0 | 12.0 |

TABLE 2-continued

Ergonomic Protective Device - Filtration Efficiency of SCB and ESR Hybrid Facemasks vs. Benchmark Masks & Respirators

| Performance Criteria | Test ID, units | SCB 300 | SCB 400 | ESR 400 | SCB 500 | ESR 500 | ZPM 700 | ESR 900 | BM1 HB/Mask | BM2 N-95 Respirator | BM3 N-99 Respirator |
|---|---|---|---|---|---|---|---|---|---|---|---|
| Flame Resistance | FR, class | 1 | 1 | 1 | 1 | 1 | 1 | 1 | 1 | — | — |
| Reference/EPD Construction | | | FIG. 8A | FIG. 8B | | FIG. 8C | FIG. 8D | FIG. 8E | | | |

Notes:
Comparative Tests followed ASTM and NIOSH protocols
SCB, ESR, ZPM are coded IDs for Devices
*EPD—Ergonomic Protective Device
**BM—Benchmark
***HB—High Barrier Table 2 illustrates the key filtration performance characteristics of various models of facemasks constructed and assembled according to the method described herein for manufacturing the Ergonomic Protective Device (EPD). All listed models are built in Medium size and feature the same three-dimensional V-shaped pleats. More specifically, the SCB 300 models are designed to meet the criteria for Mid Barrier procedural masks typically used in dental offices and low-risk areas in healthcare facilities. In cases where higher level of protection and fluid resistance is mandated, the SCB 400 and SCB 500 models will be more appropriate. ESR 400 models are specially constructed to protect the surrounding environment in clean rooms and specialty assembly areas, while the ESR 500 models are built to meet the N-95 (NIOSH) requirements for particulate respirators. In certain cases for high pathogen protection, the ZPM 700 models are assembled with fabrics treated with bioactive agents selected to entrap and inactivate the detrimental effect of typical airborne biohazards. ESR 900 models incorporate multi-layer filter media to exceed the N-99 (NIOSH) standards and can be produced in a flame retardant version. All Ergonomic Devices meet the ASTM standards for Class 1 in Flammability Tests.

The performance characteristics of benchmark products, approved for use in the United States at the present time of the tests, are listed as a reference to demonstrate the advantage of the Ergonomic Protective Device in the relevant categories. Thus, the values in Table 2 for High Barrier Surgical Mask (SM), N-95 respirator (R/N-95) and N-99 (R/N-99) are presented as an average number of two or more facemask samples from different vendors without giving any preference to a specific brand or producer. All Ergonomic Protective Devices demonstrate almost 50 percent lower values in air resistance tests while preserving or even exceeding the level of required filtration efficiency (as shown in Table 2). The Ergonomic Device also provides the overall lightest construction of N-95 and N-99 type respirators—typically 40 to 50 percent lighter than leading brands based on the simple cup-shape geometry.

Due to the lower air resistance during the inhalation and exhalation cycle, the Ergonomic Protective Device provides the same level of protection but reduces the temperature of the air in the breathing chamber by an average of 30 percent. During prolonged use, this will result in more comfortable and tolerable experience of the facemask. This effect is more prominent in humid and hot environments. At a normal room temperature of 22 C (72 F) the inner air temperature increases by only 1.5-2.0 C over 10 minutes for ESR 500, while the standard N-95 type respirators cause more than a 3.0 C increase within 10 minutes of use. At nominal 30 C temperature of the exhale air at specific test conditions, the protective masks created gradual heat buildup in the first several minutes. This test was restricted to the first 10 minutes; results: M8210 Plus—10 min/33 C; G2130 10 min/33 C; Ergonomic Safety Respirator ESR 500 10 min/32 C—30 percent improvement versus the benchmark and most popular product on the market today.

Ergonomic Protective Device with Comfortable Seals and Minimum Facial Interference In comparison with the standard cup or duckbill respirator, the Ergonomic Protective Device is designed with a narrow and soft peripheral edge, which in combination with the low tension of the donning strings, either the ear loops or neck loops, results in minimal pressure over the facial muscles. Further, the inner edges of the three-dimensional V-shaped pleats create a gentle touch with the facial skin and stabilize the protective device in a snug fit, even in the events of normal gesticulations. In comparison with standard surgical masks, the Ergonomic Protective Device covers almost a 50 percent smaller area of the wearer's face. More importantly, the breathing chamber of the device is positioned away from the nose and lips, thus maintaining a constant chamber volume that does not muffle the wearer's voice.

Further, the Ergonomic Protective Device is constructed of multi-layers of flexible and soft nonwoven fabric panels, rather than stiff pre-molded shapes. The three-dimensional V-shaped pleats are separated by short segments of multi-layered fabric which allow the device peripheral, the key sealing element of any protective device, to fit different facial profiles—more accurately, to ensure snug fit to faces with different surface (superficial) anatomy.

An important element pertinent to the device fit and seal characteristics is the type of material and length of the nosepiece. Any of the Ergonomic Protective Device models, 300 to 900 (Table 2) are made with a short nosepiece, about 6.0 sm, which bends and retains the shape of the middle part of the nose. A key advantage is to secure the device at the end of the nasal bond in the section of the upper part of the Cartilage of Septum and the Lateral Cartilage of the nose behind the soft Fibro-fatty Tissue at the lower part of the nose. This design feature allows the device to be securely attached to the wearer's face with only one neck loop affixed to the bottom of the device (as shown in FIG. 9A). In contrast, most surgical masks and respirators are made with a long nosepiece that is extended over the Zygomatic Bone, thus creating uncomfortable pressure points.

Additional improvement to the facial skin is the special pattern of the ultrasound welding around the edges and the embossed narrow line under the nosepiece. These welding patterns utilize the intrinsic properties of the thermoplastic-based fabrics to create narrow lines of concaved and convex formations along the device periphery. Thus, the device edges form flexible and soft dual-seal patterns, which are well-balanced with the force and direction of tension created by the donning loops. In a preferred embodiment, the embossed line under the nosepiece is a 1.5 mm wide solid line created by heat impulse or ultrasound welding technique. This line is positioned at the folded fabric edge over the nosepiece across the top portion of the mask. A similar welding pattern is employed at the side and bottom edges of the Device, which provides a peripheral seal and secures the three-dimensional V-shaped pleats. The most preferred welding pattern features a set of three rows of squared tips with working surface of 1×1 mm and spaced at 2 mm in each line. The two outer lines are positioned next to each other, while the tips are offset by 1.5 mm to create a checkered pattern. The third, inner, line is placed at a 2.5 mm distance from the double checkered lines. This pattern preserves the fabric softness and provides reliable welding of the fold edges at relatively low energy and pressure.

Device Interlocking Three-Dimensional V-Shaped Pleats

The main reason to create the Ergonomic Protective Device was to design and build a safety respiratory protective device with optimum performance characteristics—low air resistance, lightweight facemask with snug facial fit, and a compacted shape that will not interfere with normal articulation and vision. The combination of all these criteria, which defines the ergonomic nature of the Device, requires soft and relatively flexible materials.

First, to increase the effective surface of the breathing chamber, the filtering materials were folded in multiple pleats on the side and bottom of the device. Second, to retain the desired shape of the device and to ensure structural integrity of the breathing chamber during inhalation and exhalation at different flow rates, the device materials were secured in place by interlocking the folds into V-shaped formations. Third, the three-dimensional structure was created by the interlocking of V-shaped pleats positioned on specific intervals and having specific depths on a flat panel precursor of multi-layer filtering materials.

The three-dimensional V-shaped pleats are a unique design feature applied to the Ergonomic Protective Device for the first time. These three-dimensional V-shaped pleats have multiple purposes in retaining of device integrity under the cycling forces forward—backward during normal breathing and to ensure optimum filtering material condensed around an ergonomic shape to fit human faces with different surface anatomy. Moreover, the intersecting three-dimensional V-shaped pleats provide the fundamental structure to build a device with more than twice SVR value in comparison with popular simple shaped masks and respirators.

In the filtration industry, pleating of the filter material is practiced to produce various devices with increased surface area. However, all common techniques are based on two-dimensional folding patterns for flexible or semi-rigid materials and require additional supporting elements. Although such structures are economic and suitable for industrial and household filtration systems, these two-dimensional folding patterns are not an optimum solution to fit the complexity and uniqueness of the human face. The alternative solutions of rigid materials used in the simple shape protective facemasks create design and performance constrains due to size, weight, or fit of the finished device.

An ergonomic protective air filtration device includes an arrangement of at least two layers of an air permeable material, the arrangement having a periphery, an inner side and an outer side; a plurality of three-dimensional V-shaped pleats extending from the periphery and into the arrangement of layers to form a convex body; and a retaining means engaging the convex body of the device to secure the device to a face of a wearer and to create a breathing chamber on the inner side of the device. In an embodiment, the arrangement is a stack of at least two layers of the air permeable material. In an embodiment, the plurality of three-dimensional V-shaped pleats intersect with adjacent three-dimensional V-shaped pleats.

An ergonomic protective air filtration device includes a stack of at least two layers of an air permeable material, the stack forming a body, a periphery, and a back; a plurality of intersecting three-dimensional V-shaped pleats extending from the periphery and into the stack of layers, so the back of the device defines a breathing chamber adapted to cover a mouth and a nose of the wearer; and a retaining means engaging the body of the device to secure the device to a face of the wearer and to create the breathing chamber.

In an embodiment, a bottom edge, a right-side edge and a left-side edge along the periphery, wherein the bottom edge comprises a bottom right-side pleat located on the right side of the bottom edge and a bottom left-side pleat located on the left side of the bottom edge. In an embodiment, the bottom right-side pleat intersects with a corresponding pleat on the right-side edge and the bottom left-side pleat intersects with a corresponding pleat from the left-side edge. In an embodiment, a second bottom left-side pleat and a second bottom right-side pleat, the second bottom right-side pleat intersecting with a corresponding second pleat on the right-side edge and the second bottom left-side pleat intersecting with a corresponding second pleat from the left-side edge.

In an embodiment, the intersecting bottom side pleats and side edge pleats form specific angles at a point of intersection.

In an embodiment, the air permeable material is a fabric. In an embodiment, an external layer made of an air permeable spunbond fabric, a filtering layer made of an air permeable meltblown fabric, and an internal layer made of an air permeable spunbond fabric.

In an embodiment, the breathing chamber is delimited by the back of the device, a lower half of the nose, the lips and the mouth, an anterior part of the jaw, and a line behind the nasolabial sulcus of the wearer.

In an embodiment, a fire resistant coating applied to at least the outer layer. In an embodiment, the device provides protection against contaminated droplets, fluid splashes, solid particulates, pathogenic microorganisms, or aerosoled air pollutions. In an embodiment, a bioactive agent applied to one or more layers of the device to provide enhanced protection against detrimental microorganisms dispersed in droplets or aerosols. In an embodiment, a surface tension modifier applied to one or more layers of the device. In an embodiment, a low molecular weight polymeric material applied to one or more layers of the device to enhance surface tension. In an embodiment, selected layers or all fabric layers are treated with special agents during the fiber forming process or applied on the fabric surface.

In an embodiment, the breathing chamber has a surface to volume ratio from about 1 to about 4. In an embodiment, the breathing chamber has a surface to volume ratio of about 2. In an embodiment, the breathing chamber has a surface weight ratio from about 20 to about 60. In an embodiment, the breathing chamber has a surface weight ratio of about 44.

In an embodiment, the device has a low air resistance. In an embodiment, the plurality of three-dimensional V-shaped pleats create a compact and lightweight breathing chamber characterized by 50% lower air resistance than similar devices having simple geometric shapes. In an embodiment, the plurality of three-dimensional V-shaped pleats create a compact and lightweight breathing chamber made of soft and flexible materials, thus providing a snug peripheral seal and fit of the device to human faces with different surface anatomy. In an embodiment, a peripheral seal of the device with the face allows natural facial articulation and speech.

The sot and flexible materials of the device permit the creation of a peripheral seal between the device and the face of a wearer.

In an embodiment, the device has a low profile that does not restrict the downward vision of the wearer.

A method for constructing an ergonomic protective air filtration device includes stacking at least two layers, each made of an air permeable material, into a stack forming a body, a periphery, and a back; forming, with the stack of layers, a plurality of three-dimensional V-shaped pleats extending from the periphery, so that the back of the device defines a breathing chamber adapted to cover a nose and a mouth of a wearer; joining the layers of the stack and the pleats at the periphery of the device and at a plurality of specific points throughout the stack of layers; and affixing a retaining means to the periphery of the device for retaining the device to a face of the wearer and creating a breathing chamber.

Numerous modifications may be made to the embodiments above without departing from the scope of the presently disclosed embodiments. All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art.

What is claimed is:

1. An ergonomic protective air filtration device comprising:

a partially laminated arrangement of at least two layers of an air permeable soft fabric material, the laminated arrangement having a periphery, an inner side an outer side, a left side, a right side, and a bottom side;

a symmetrical pattern of three-dimensional V-shaped pleats extending from the left, right, and bottom sides of the periphery, wherein the pleats intersect in a symmetrical step-like and angled pattern in a central portion of the device to form a semi-rigid but flexible convex body having a pyramidal shape when viewed from the outer, inner, left, and right sides, and having a triangular contour when viewed from the bottom side, and wherein said symmetrical pattern of three-dimensional V-shaped pleats forms a three-pointed Y-configuration on the outer side.

2. The ergonomic protective air filtration device of claim 1, wherein a breathing chamber having a stepped pyramidal shape is constructed to contact a wearer's face only at the periphery in the regions of the lower half of the nose, the anterior part of the jaw, and a line behind the nasolateral sulcus;

wherein the three-pointed Y-configuration spans over the convex shape of the breathing chamber and provides structural support to the left, right, and bottom sides;

wherein the symmetrical pattern of three-dimensional V-shaped pleats allows the device to be flat-folded in half;

wherein the device is formed by a process comprising folding a trapezoidal form of said soft fabric material into said convex body with pyramidal shape;

wherein the convex body and inner side of said breathing chamber are spaced away from the wearer's lips and nasal orifices; and wherein a retaining means engages the convex body to secure the device to the wearer's face and provides a close facial seal at the device periphery.

3. The ergonomic protective air filtration device of claim 1 or claim 2, wherein said soft fabric material is an air permeable woven or non-woven material;

wherein the symmetrical pattern of three-dimensional V-shaped pleats perpendicular to the bottom edge of the convex body intersect in pairs the symmetrical pattern of three-dimensional V-shaped pleats from the side edges of the convex body by forming a sharp angle between 45 and 75 degrees; and wherein intersecting sharp edges of the V-shaped pleats are arranged in a symmetrically angled pattern of about 60 degrees on left, right, and top sides of the convex body.

4. An ergonomic protective air filtration device which when donned by a wearer forms a breathing chamber defined by a space between the wearer's face and an inner side of a symmetrical pattern of intersecting three-dimensional V-shaped pleats extending from a periphery and into a central portion of the device;

wherein the breathing chamber has a concave pyramidal shape, is flexible, and has a semi-rigid structure to maintain a three-dimensional configuration; and wherein the device contacts the wearer's face only at the periphery of the device and at the lower half of the wearer's nose, the anterior part of the wearer's jaw, and a line behind the wearer's nasolabial sulcus.

5. The ergonomic protective air filtration device of claim 4, further comprising a bottom edge, a right-side edge and a left-side edge along the periphery, wherein the bottom edge comprises one or more bottom right-side pleats located on the right side of the bottom edge and one or more bottom left-side pleats located on the left side of the bottom edge; and wherein the bottom and side edges are part of a stepped pyramidal structure.

6. The ergonomic protective air filtration device of claim 4, further comprising a right-side edge and a left-side edge along the periphery, wherein the right-side edge comprises one or more right-side pleats and the left-side edge comprises one or more left-side pleats, and wherein the right-side and left-side edges are part of a stepped pyramidal structure.

7. The ergonomic protective air filtration device of claim 5 or claim 6, wherein the bottom right-side pleat intersect at an angle of about 60 degrees and in a symmetrical pattern with a corresponding pleat on the right-side edge and the bottom left-side pleat intersect at an angle of about 60 degrees with a corresponding pleat from the left-side edge, wherein the right side of the device intersects at an angle of approximately 90 degrees at a middle line with the left side of the device, and wherein both the right and left sides of the device intersect at an anile of approximately 90 degrees with the bottom side of the device.

8. The ergonomic protective air filtration device of claim 7, further comprising two, three, four, or five bottom left-side pleats and two, three, four, or five bottom right-side pleats, and wherein the second, third, fourth, or fifth bottom right-side pleats intersect with corresponding second, third, fourth, or fifth pleats on the right-side edge, and the second, third, fourth, or fifth bottom left-side pleats intersect with corresponding second, third, fourth, or fifth bottom left-side pleats on the left-side edge.

9. The ergonomic protective air filtration device of claim 8, wherein the intersecting bottom side pleats and side edge pleats form angles of between 45 degrees and 75 degrees at a point of intersection, and wherein the right, left, and bottom sides of the device intersect at an angle of approximately 90 degrees in a middle line and two bottom diagonals of the device.

10. The ergonomic protective air filtration device of claim 9, wherein the breathing chamber is delimited during use by the back of the device, a lower half of the nose, the lips and the mouth, an anterior part of the jaw, and a line behind the nasolabial sulcus of the wearer, and wherein the breathing chamber periphery is a trapezoid.

11. The ergonomic protective air filtration device of claim 4 or claim 10, wherein:

(i) the breathing chamber has a surface to volume ratio from about 1 to about 4; or (ii) the breathing chamber has a surface to weight ratio from about 20 to about 60; or (iii) the device has it low profile that does not restrict the downward vision of the wearer; or (iv) a peripheral flexible seal of the device allows natural facial articulation and speech.

12. The ergonomic protective air filtration device of claim 1 or claim 4, further comprising:

(i) a fire resistant agent incorporated into polymer fibers of at least an outer layer during a fabric formation process; or (ii) a bioactive agent incorporated into polymer fibers of at least an outer layer during a fabric formation process or applied to one or more layers of the device to provide enhanced protection against detrimental microorganisms dispersed in droplets or aerosols; or (iii) a low molecular weight polymeric material or chemical agent which functions as a surface tension modifier, is incorporated into polymer fibers of one or more layers of the device, and is incorporated during a fabric formation process; and (a) wherein the device is made with nano-grade filter material; or (b) wherein the device is made using a pre-arranged sequence of untreated layers and layers treated with a surface modifying agent that results in a hydrophobic-hydrophilic type of barrier; or (c) wherein the device provides protection against contaminated droplets, fluid splashes, solid particulates, pathogenic microorganisms, or aerosoled air pollutants; or (d) wherein the device has low air resistance.

13. The ergonomic protective air filtration device of claim 4, wherein the air permeable material is a composite non-woven fabric.

14. A method for constructing a pleated ergonomic protective air filtration device, the method comprising the steps of:

(i) laminating at least two layers of air permeable material or non-woven fabric by tacking or embossing a dotted pattern along pleat edges and a periphery of the device;

(ii) forming the laminate into a stepped pyramidal shape by symmetrical arrangement of intersecting three-dimensional V-shaped pleats extending from the periphery and forming angles of about 60 degrees at the intersection points, whereby right, left, and bottom sides of the device intersect at an angle of approximately 90 degrees at a middle line and two bottom diagonals of the device, forming a three-pointed Y-configuration on a front side of the device;

(iii) joining edges of the pleats at the periphery of the device at a plurality of points throughout the periphery, whereby a semi-rigid but flexible breathing chamber having a stepped pyramidal shape is formed; and (iv) affixing retaining means for retaining the device on a wearer's face to the periphery of the device.

15. A method for constructing an ergonomic protective air filtration device having a stepped pyramidally shaped structure by sequential folding of intersecting V-shaped three-dimensional pleats, the method comprising the steps of:

(i) laminating at least two layers of air permeable material or non-woven fabric by tacking or embossing a dotted pattern along pleat edges and a periphery of the device;

(ii) folding a bottom pleat on a right side of a bottom edge of the laminate, and folding a bottom pleat on a left side of a bottom edge of the laminate;

(iii) folding a pleat on a right-side edge and folding a pleat on a left-side edge, such that the bottom pleat of the right side of the bottom edge intersects with the pleat on the right-side edge, and such that the bottom pleat of the left side of the bottom edge intersects with the pleat on the left-side edge;

(iv) forming a three-dimensional stepped pyramidally shaped structure by sequential folding of a plurality of intersecting V-shaped three-dimensional pleats, and forming angles of about 60 degrees at intersection points, whereby right, left, and bottom sides of the device intersect at an angle of approximately 90 degrees in a middle line and two bottom diagonals of the device, forming a three-pointed Y-configuration on a front side of the device;

(v) joining edges of the pleats at the periphery of the device at a plurality of points throughout the periphery, whereby a semi-rigid but flexible breathing chamber having a stepped pyramidal shape is formed; and (vi) affixing retaining means for retaining the device on a wearer's face to the periphery of the device.

* * * * *